United States Patent
Leigh et al.

(10) Patent No.: US 8,570,040 B2
(45) Date of Patent: Oct. 29, 2013

(54) MRI IMAGE DISTORTION REDUCTION FOR MRI IMAGES OF A RECIPIENT HAVING AN IMPLANTABLE MEDICAL DEVICE

(75) Inventors: C. Roger Leigh, East Ryde (AU); Ruben Peters, Kingsford (AU)

(73) Assignee: Cochlear Limited, Macquarie University, NSW (AU)

( * ) Notice: Subject to any disclaimer, the term of this patent is extended or adjusted under 35 U.S.C. 154(b) by 408 days.

(21) Appl. No.: 12/982,704

(22) Filed: Dec. 30, 2010

(65) Prior Publication Data
US 2012/0169336 A1  Jul. 5, 2012

(51) Int. Cl.
*G01R 33/44* (2006.01)

(52) U.S. Cl.
USPC .......................... 324/309; 324/307

(58) Field of Classification Search
USPC ................... 324/307, 309; 600/407
See application file for complete search history.

(56) References Cited

U.S. PATENT DOCUMENTS

2007/0100226 A1* 5/2007 Yankelevitz et al. ......... 600/407
2010/0315082 A1* 12/2010 Garwood et al. ............ 324/307

* cited by examiner

*Primary Examiner* — Patrick Assoud
*Assistant Examiner* — Rishi Patel
(74) *Attorney, Agent, or Firm* — Kilpatrick, Townsend & Stockton, LLP.

(57) ABSTRACT

A method for generating a new set of MRI images of a region of a recipient in which an implanted medical device having magnetic properties is located. The method includes scanning a plurality of scan slices of the recipient with an MRI machine set at a first fat shift direction to generate a first set of MRI images and rescanning the plurality of scan slices with a fat shift direction different than the first fat shift direction to obtain a second set of MRI images. At least one of the MRI images of the first set and the second set including an artifact resulting from the implanted medical device. The method further includes comparing respective artifacts of the MRI images of the first and second sets, and selecting one of the compared MRI images based on the distortion to the respective MRI image created by the respective artifact.

15 Claims, 21 Drawing Sheets

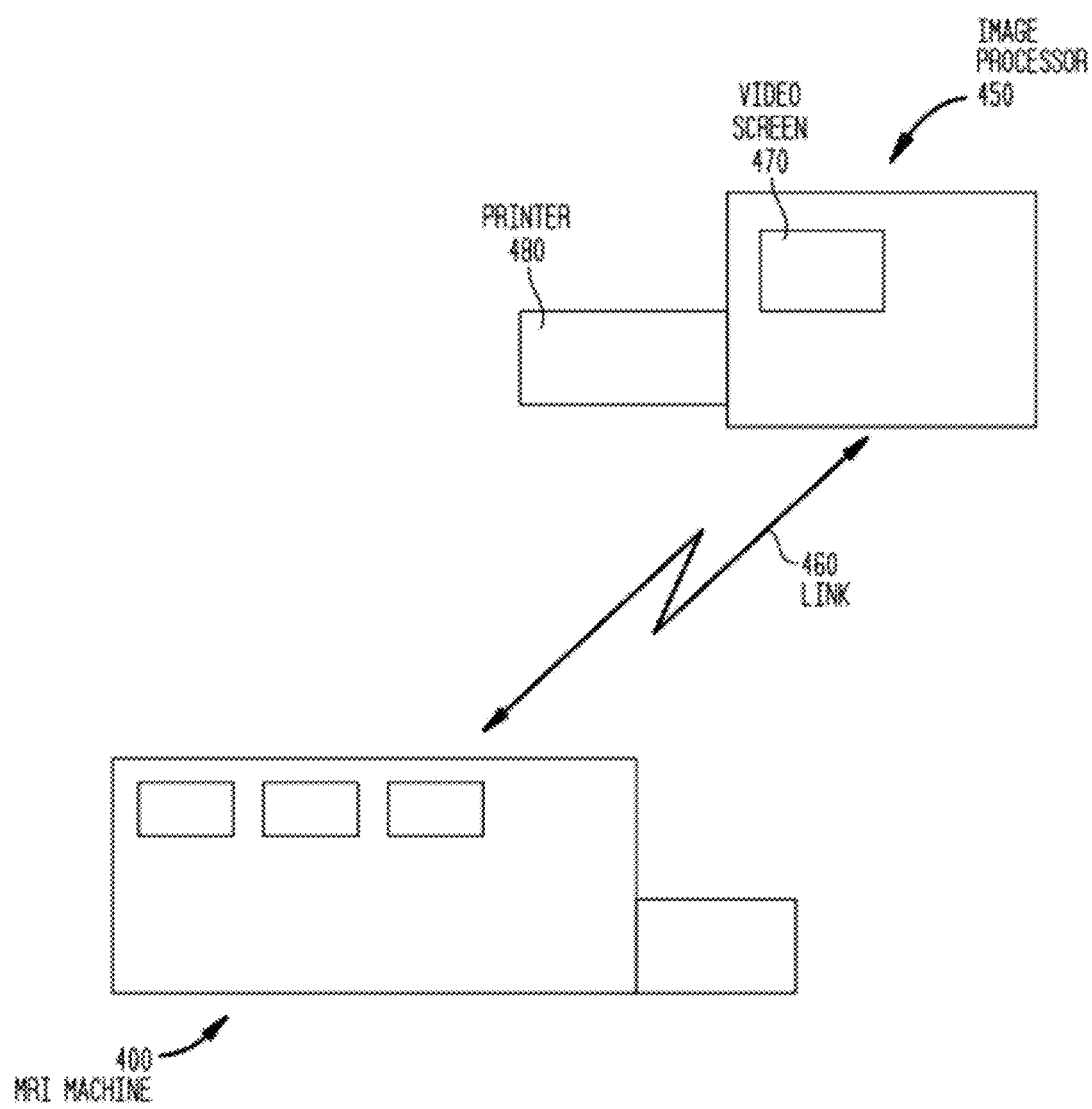

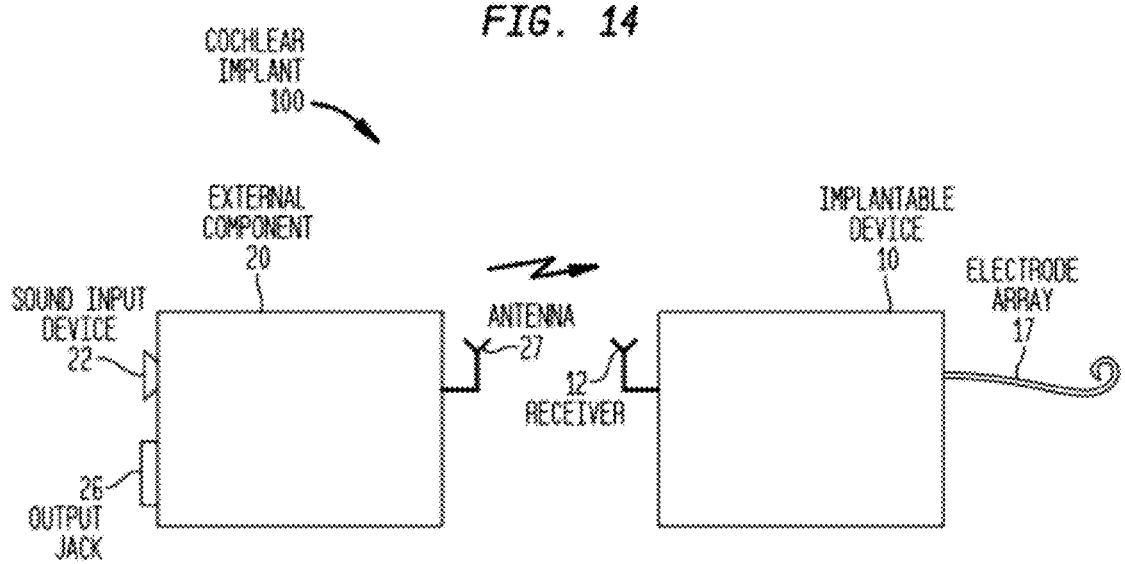
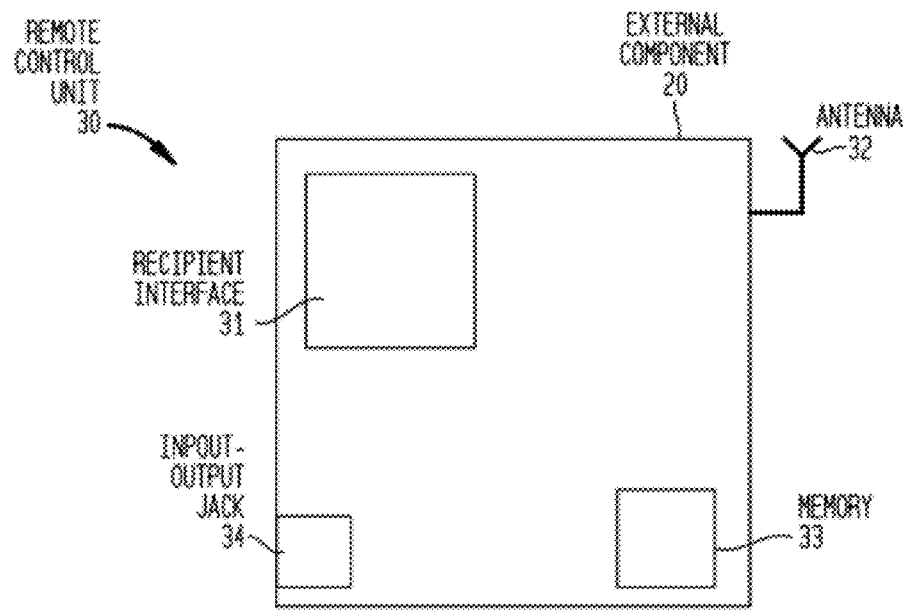

MRI IMAGE DISTORTION REDUCTION FOR MRI IMAGES OF A RECIPIENT HAVING AN IMPLANTABLE MEDICAL DEVICE

BACKGROUND

1. Field of the Invention

The present invention relates generally to Magnetic Resonance Imaging (MRI), and more particularly, to reducing distortion in Magnetic Resonance Imaging (MRI) images of a recipient caused by the presence of a implantable medical device in the recipient.

2. Related Art

Various implants can be implanted into a recipient to provide a medical benefit. Such implants may range from, on the one hand, passive devices such as screws that are utilized to adhere bones together to, on the other hand, active implants, such as, for example, hearing prostheses such as cochlear implants that perform an active function such as stimulating the cochlea of a recipient to enhance hearing. Other exemplary active devices include devices for regulating hormones or regulating cardiac activity.

A range of active implantable medical devices apply electrical energy to tissue of a recipient to stimulate that tissue. Examples of such implants include pacemakers, auditory brain stem implants (ABI), functional electrical stimulators and cochlear implants. Other implantable medical devices perform other functions such as monitoring various functions of the recipient's body such as glucose level, and others can be used to administer drugs internally.

A cochlear implant allows for electrical stimulating signals to be applied to the auditory nerve of a recipient, causing the brain to perceive a hearing sensation approximating the natural hearing sensation, thereby enhancing hearing. These stimulating signals may be applied by an array of electrodes implanted into the recipient's cochlea.

The electrode array is connected to a stimulator that generates the electrical signals for delivery to the electrode array. The stimulator in turn is operationally connected to a sound processor (which may be implanted in the recipient, or which may be located externally to the recipient, communication with the stimulator being via a transcutaneous inductance link) which is in signal communication with a microphone. The microphone receives audio signals from the environment. The sound processor processes these signals to generate control signals for the stimulator.

It is not uncommon for a recipient of an implantable medical device to undergo subsequent medical treatment or investigations related to the implantable medical device or the recipient's condition. Certain post-operative investigations utilize Magnetic Resonance Imaging (MRI).

MRI relies on the application of a strong magnetic field to a recipient's body to generate images of tissue and bone structure. The magnetic field aligns protons (hydrogen atoms) within the recipient's body. These atoms are then be excited into resonance by an applied RF field. When the RF field is removed, the atoms release energy as they exit their excited state. This release of energy is detected by a receiver and utilized to create an MRI image.

The presence of materials within the applied magnetic field which have a magnetic property may distort the magnetic field, causing artifacts in the resulting MRI image. Such artifacts may obscure features, resulting in misdiagnosis of the patients' conditions such as, for example, tumors, that are not able to be resolved in the image due to the distortion.

For example, a cochlear implant may contain a transformer which includes a small quantity of ferromagnetic material. Other materials such as the housing and/or the electronics of the stimulator/receiver of the cochlear implant have an adverse effect.

The human body has a magnetic permeability similar to that of water. Implantable medical devices such as cochlear implants typically have components with permeability different to that of water (e.g., transformer cores, housings, etc.). In the past, designers of implantable medical devices have attempted to address this problem by designing the medical device implant with a minimum of ferromagnetic materials. Alternatively, designers utilized additional components made from materials having low magnetic permeability to counterbalance components made from materials having high magnetic permeability. Some designs rely upon devices having ferromagnetic components that are removable through a minor medical procedure prior to undergoing an MRI scan.

SUMMARY

According to one aspect of the present invention, there is a method for generating a new set of MRI images of a region of a recipient in which an implanted medical device having magnetic properties is located. The method comprises scanning a plurality of scan slices of the recipient with an MRI machine set at a first fat shift direction resulting in a first set of MRI images including a plurality of MRI images respectively corresponding to the plurality of scan slices, wherein the first set of MRI images comprises at least one MRI image having an artifact resulting from the implanted medical device, rescanning at least some of the plurality of scan slices with the MRI machine set at a second fat shift direction different than the first fat shift direction resulting in a second set of MRI images including at least one MRI image having an artifact resulting from the implanted medical device, comparing a respective artifact of an MRI image corresponding to a first scan slice of the recipient of one of the first set of MRI images and the second set of MRI images to a respective artifact of an MRI image corresponding to the first scan slice of the recipient of the other of the first set of MRI images and the second set of MRI images, and selecting one of the compared MRI images based on the distortion to the respective MRI image created by the respective artifact.

According to another aspect of the present invention, there is a method of obtaining a new MRI image of a recipient of an implantable medical device, the method comprises generating a first MRI image by scanning a first scan slice of the recipient with an MRI machine set at a first fat shift direction, generating a second MRI image by repeating the scan of the first scan slice with the MRI machine set at a second fat shift direction, approximately opposite to the first fat shift direction, and generating a new MRI image based on the first MRI image and the second MRI image.

According to another aspect of the present invention, there is a method for generating a set of MRI images of a region of a recipient in which an implanted medical device having magnetic properties is located, the method comprises obtaining a first set of MRI images of the region of the recipient, the first set of MRI images comprising a plurality of MRI images obtained by MRI scanning a first plurality of scan slices of the recipient using a first fat shift direction, wherein at least one MRI image of the first set of MRI images includes an artifact resulting from the implanted medical device, obtaining a second set of MRI images, the second set of MRI images comprising a plurality of MRI images obtained by MRI scanning a second plurality of scan slices of the recipient using a second fat shift direction approximately opposite to the first fat shift direction, wherein at least a first scan slice of the second plurality of respective scan slices is the same scan slice as a scan slice of the first plurality of respective scan slices, and generating a third set of MRI images by selecting a sub-set of MRI images from the first set of MRI images and a sub-set of MRI images from the second set of MRI images and combining the sub-sets, wherein the third set includes an MRI image corresponding to the first scan slice, and wherein the size of the artifact of an MRI image of the third set corresponding to the first scan slice is reduced as compared to the size of the artifact of the MRI image of the first set of the first scan slice or the size of the artifact of the MRI image of the second set of the first scan slice.

BRIEF DESCRIPTION OF THE DRAWINGS

Embodiments of the present invention are described below with reference to the attached drawings, in which:

FIG. 1C shows a block diagram of an MRI machine in communication with an image processor usable in an embodiment of the present invention;

FIG. 14 shows a cochlear implant system with instructions stored thereon to perform the method of FIGS. 10A, 10B and/or 11;

FIG. 15 shows a remote control unit for use in the cochlear implant system with instructions stored thereon to perform the method of FIGS. 10A, 10B and/or 11 according to an embodiment of the present invention.

DETAILED DESCRIPTION

Some exemplary embodiments of the present invention include methods, apparatuses, systems and algorithms for reducing the above-discussed artifact in a set of MRI images. Exemplary methods include generating a first set of images using an MRI machine using a first fat shift direction. The scans are repeated for the same MRI slices of the recipient using a second fat shift direction, approximately opposite to the first fat shift direction. The first and second sets of MRI images will have the artifact displaced with respect to each other. A set of MRI images is then generated by replacing some of the images of the various sets with new images of the same respective MRI slice. In an exemplary embodiment, MRI images from the first and second sets are selected and then combined into a new set of MRI images such that the artifact appearing on the images is reduced.

Some exemplary embodiments of the present invention also include obtaining a new MRI image from a selection of one of two or more MRI images generated using approximately opposite fat shift directions, the new MRI image containing a reduced artifact.

The following abbreviations are used herein in the description of some embodiments of the present invention:

| | |
|---|---|
| T2W_FFE | T2 weighted _ fast field echo |
| T1W_SE | T1 weighted _ spin echo |
| PDW-TSE | Proton density weighted - turbo spin echo |
| T2W-TSE | T2 weighted - turbo spin echo |
| PDW_FLAIR | Proton density weighted _ fluid attenuation inversion recovery |

Figure 1A:
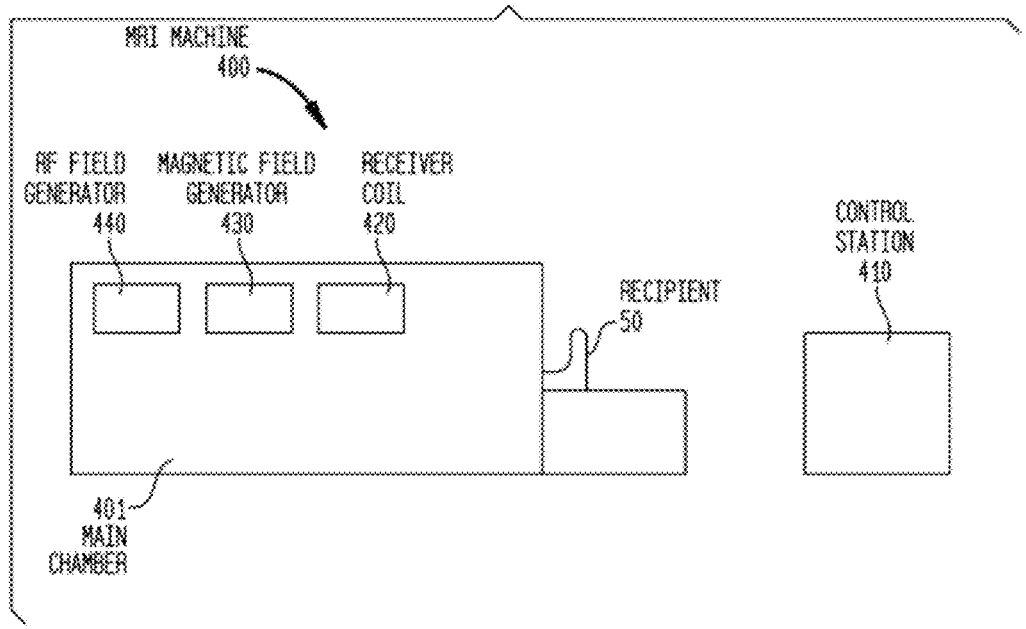
FIG. 1A shows a block diagram of an MRI machine used in an embodiment of the present invention.

FIG. 1A is a representative block diagram of some components of an MRI machine 400 referenced herein. Shown in FIG. 1A is main chamber 401, which, in some embodiments, is configured as a large tubular chamber in which the recipient 50 who is to be scanned with the MRI machine is placed. In the view of FIG. 1A, only the feet of the recipient 50 are visible, the rest of the recipient 50 being enclosed in the main chamber 401. Also shown are magnetic field generator 430, receiver coil (also referred to as receiver) 420 and radio frequency (RF) field generator 440. It will be understood that the functionality of at least some of these components may be variously integrated into a single component. Indeed, it is noted that some embodiments of the present invention are practiced with any type/configuration of an MRI machine that will permit the present methods disclosed herein for artifact reduction and variations thereof to be implemented.

During operation of the MRI machine 400, magnetic field generator 430 and RF field generator 440 is controlled by control station 410. In some cases, a human operator controls the operation of the MRI machine 400 from control station 410. It will also be appreciated that some or all of the MRI machine's 400 operations are automated and function in accordance with machine-readable instructions.

Figure 1B:
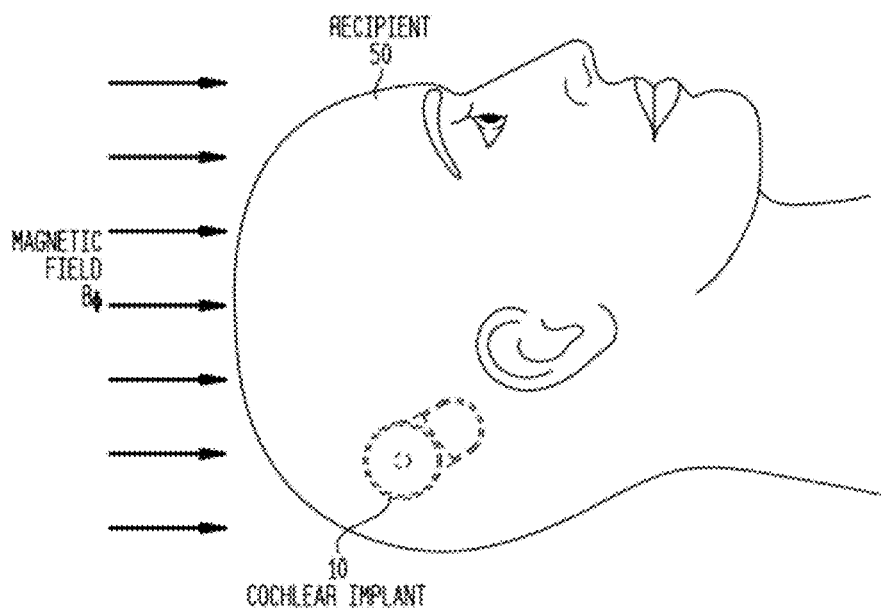
FIG. 1B shows an illustration of a recipient with a cochlear implant (CI) being positioned for an MRI scan in an embodiment of the present invention.

FIG. 1B depicts a schematic of the recipient's 50 head when located inside the main chamber 401 of FIG. 1A. In this case, the recipient 50 has a implantable medical device such as a cochlear implant 10 implanted in the recipient's 50 head.

FIG. 1C depicts an image processor 450 in communication with the MRI machine 400 via a link 460. Link 460 may be a wireless link, wired link, or any type of link that permits MRI images or data from which MRI images may be generated to be transmitted from MRI machine 400 to image processor 460. Image processor 450 includes a video screen 470 on which the image processor 460 may display MRI images. Image processor 460 further includes a printer 480 from which print-outs of the MRI images may be obtained. Additional features of the image processor 450 will be described below.

In operation, MRI machine 400 generates a large magnetic field $B_\Phi$ which in the schematic depicted in FIG. 1B is directed horizontally from left to right. This magnetic field $B_\Phi$ is generated by magnetic field generator 430 as described above.

In most volumes of tissue, the magnetic vector sum of all hydrogen nuclei (also referred to as the Net Magnetic Vector (NMV)) should be zero, as the spin vectors of all protons are randomly oriented. However, the application of magnetic field $B_\Phi$ causes magnetic moments of the protons in the hydrogen atoms of the recipient's tissue to align parallel (including anti-parallel) to the magnetic field $B_\Phi$. As a result of a quantum phenomenon known as Zeeman interaction, there should be a slight excess of the protons' magnetic moments oriented parallel to the magnetic field $B_\Phi$. This results in a macroscopic net magnetization, $M_O$, aligned parallel to $B_\Phi$. Furthermore, due to interactions between $B_\Phi$ and the positively charged nucleus of the hydrogen atoms that are spinning, the protons within the magnetic field should precess about the direction of the magnetic field $B_\Phi$.

A high amplitude radio frequency (RF) pulse is applied to the recipient 50 in a direction 90° from $B_\Phi$, in order to generate a magnetic resonance (MR) signal, at the same and/or about the same frequency at which the hydrogen nuclei precess. In some embodiments, this causes the hydrogen nuclei to resonate with the applied RF signal. However, nuclei other than hydrogen may not resonate, as their gyromagnetic ratios are different.

In some embodiments of the present invention, two phenomena occur at resonance: energy absorption and phase coherence. With respect to energy absorption, the hydrogen nuclei absorb energy from the RF pulse, which alters the distribution of magnetic moments aligned parallel and anti-parallel to the magnetic field. This has the effect of rotating the NMV into a transverse plane. With respect to phase coherence, the RF pulse causes the magnetic moments of all or substantially all hydrogen nuclei to precess in phase/about in phase with each other, which means the NMV precesses (now in the transverse plane).

As the NMV rotates in the transverse plane it induces a voltage signal in the receiver coil/receiver 420, positioned close to the recipient 50. This phenomenon is referred to as free induction decay, and the detected voltage is the fundamental MR signal.

Many fine variations of parameters of the magnetic field $B_\Phi$ and RF signal are used to control the types of received signals to produce desired effects in the generated image, including controlling the depth of the image, the type of tissue targeted and the contrast between different tissue types.

The scans generated by the MRI machine 400 result in a set of images representing "slices" at different depths of a region of the recipient 50. In some embodiments of the present invention, the thickness of the slices are varied from, for example, about 1 mm or less to about 5 mm or more. In this way, the set of images, when combined, provide a detailed "volume" image of the portion of the recipient that is scanned with the MRI machine 400.

Accordingly, an embodiment of the present invention utilizes an MRI machine wherein some and/or all of the above-mentioned phenomena are exhibited during scanning utilizing the MRI machine.

Figure 2A:
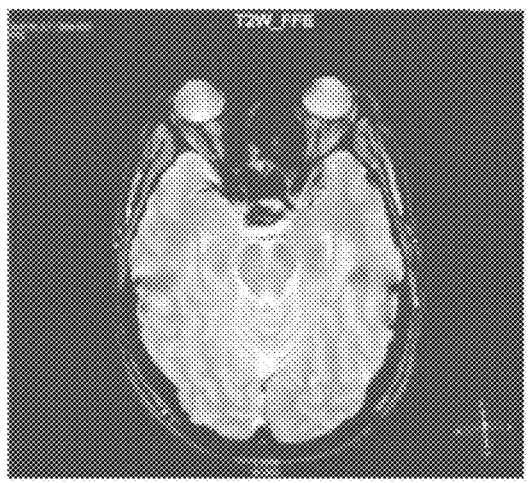
FIG. 2A shows an $8^{th}$ slice of 22 slices of an MRI scan of a recipient with no CI using a T2W_FFE sequence.
Figure 2B:
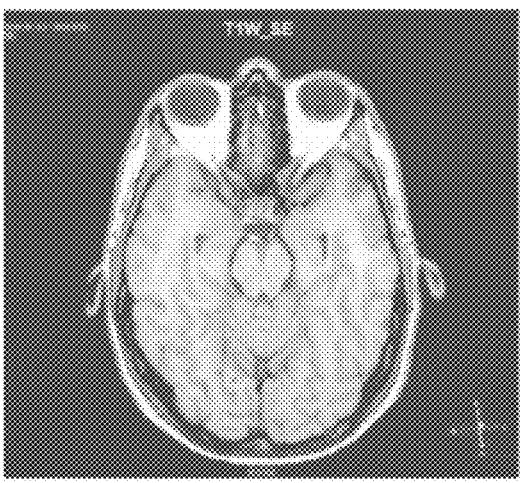
FIG. 2B shows an $8^{th}$ slice of 22 slices of an MRI scan of a recipient with no CI using a T1W_SE sequence.
Figure 2C:
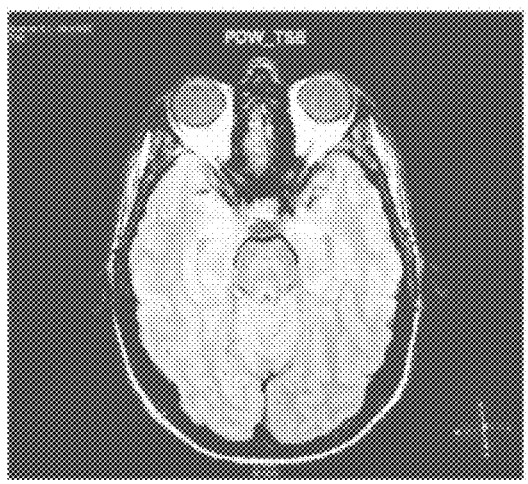
FIG. 2C shows an $8^{th}$ slice of 22 slices of an MRI scan of a recipient with no CI using a PDW-TSE sequence.
Figure 2D:
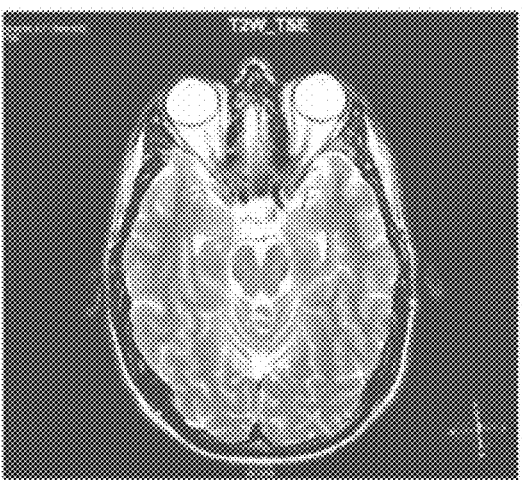
FIG. 2D shows an $8^{th}$ slice of 22 slices of an MRI scan of a recipient with no CI using a T2W-TSE sequence.
Figure 2E:
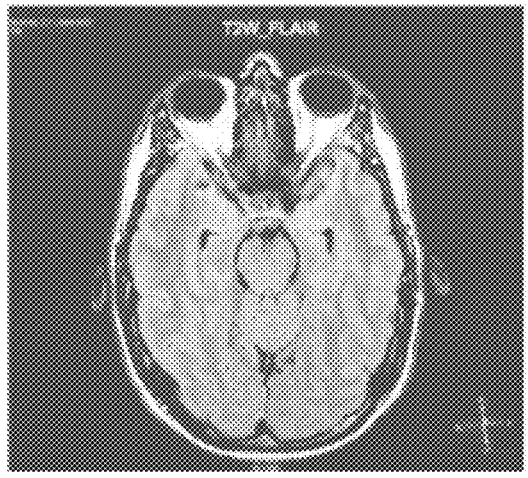
FIG. 2E shows an $8^{th}$ slice of 22 slices of an MRI scan of a recipient with no CI using a P2W_FLAIR sequence.

FIGS. 2A to 2E show various MRI images of a patient's head resulting from a series of scans. Each MRI image shown in FIGS. 2A-2E is the 8$^{th}$ slice of 22 slices forming a set of images and each MRI image shown in FIGS. 2A-2E is generated using a different scanning sequence, which corresponds to variations in different parameters. For example, FIG. 2A shows an image obtained using a T2W_FFE sequence, FIG. 2B shows an image obtained using a T1W_SE sequence, FIG. 2C shows an image obtained using a PDW_TSE sequence, FIG. 2D shows an image obtained using a T2W_TSE sequence and FIG. 2E shows an image obtained using a PDW_FLAIR sequence. Table 1 below presents exemplary parameters of the MRI machine that may be used to generate the images of FIGS. 2A to 2E. The images of FIGS. 2A to 2E may be obtained by scanning a region of the recipient's head using a Philips Intera 1.5 T MRI scanner with parameters set as presented in Table 1 below.

TABLE 1

| | |
|---|---|
| Main Field Strength (T) | 1.5 |
| Main Field Inhomogeneities (ppm) | <0.27 |
| Maximum gradient amplitude (mT m$^{-1}$) | 33 |
| Gradient slew rate (mT m$^{-1}$ ms$^{-1}$) | 80 |

Tables 2 to 6 below present exemplary specific values for various parameters usable to obtain the different images of FIGS. 2A to 2E, respectively. The images of FIGS. 2A to 2E were obtained using MRI machine parameters corresponding to Series 1 presented in the tables.

TABLE 2

T2W_FFE (5.1.1 -Gradient Echo Sequence)

| Controlled Parameters | | Varied Parameters | Series 1/2 | Series 3 | Series 4 | Series 5 |
|---|---|---|---|---|---|---|
| Voxel (mm) | 0.85 × 1.05 × 5 | Receive Bandwidth hz/pix | 108.7 | 108.7 | 353.5 | 108.7 |
| Slice Thickness/Gap (mm) | 5/1.2 | Phase Encoding Dir. | RL | AP | RL | RL |
| Acquisition matrix (pix) | 272 × 218 | Fat Shift Direction | P | L | P | A |
| TE(ms) | 23 | Scan Time (m:s) | 2:28 | 2:30 | 4:24 | 2:28 |
| TR(ms) | 677 | | | | | |
| Flip Angle (deg) | 18 | | | | | |
| Whole body SAR | <2.0 W/kg | | | | | |
| Voxel Volume (mm$^3$) | 4.46 | | | | | |

TABLE 3

T1W_SE (5.1.2 - Conventional Spin Echo, T1 Weighted)

| Controlled Parameters | | Varied Parameters | Series 1/2 | Series 3 | Series 4 | Series 5 |
|---|---|---|---|---|---|---|
| Voxel (mm) | 0.8 × 1.05 × 5 | Receive Bandwidth hz/pix | 108.7 | 108.7 | 358.7 | 108.7 |
| Slice Thickness/Gap (mm) | 5/1.2 | Phase Encoding Dir. | RL | AP | RL | RL |
| Acquisition matrix (pix) | 272 × 218 | Fat Shift Direction | P | L | P | A |
| TE(ms) | 15 | TR(ms) | 597 | 597 | 526 | 597 |
| Flip Angle (deg) | 69 | Scan Time (m:s) | 2:11 | 2:11 | 3:50 | 2:11 |
| Whole Body SAR | <1.9 W/kg | | | | | |
| Voxel Volume (mm$^3$) | 4.20 | | | | | |

TABLE 4

PDW_TSE (5.1.3 - Proton Density Weighted, Fast Spin Echo)

| Controlled Parameters | | Varied Parameters | Series 1/2 | Series 3 | Series 4 | Series 5 | Series 6 |
|---|---|---|---|---|---|---|---|
| Voxel (mm) | 0.55 × 0.68 × 5 | Receive Bandwidth hz/pix | 127 | 127 | 568.2 | 127 | 296.8 |
| Slice Thickness/Gap (mm) | 5/1.2 | Phase Encoding Dir. | RL | AP | RL | RL | RL |
| TE (ms) | 30 | Fat Shift Direction | P | L | P | A | P |
| TR (ms) | 1800 | ETL | 3 | 3 | 3 | 3 | 8 |
| Flip angle (deg) | 90 | Echo Spacing/Shot (ms) | 15/45 | 15/45 | 15/45 | 15/45 | 6.7/53 |
| Whole Body SAR | <1.4 W/Kg | Voxel (mm) | 0.55 × 0.68 × 5 | 0.55 × 0.68 × 5 | 0.65 × 0.82 × 5 | 0.55 × 0.68 × 5 | 0.6 × 0.76 × 5 |
| | | Acquisition matrix (pix) | 420 × 336 | 420 × 336 | 352 × 282 | 420 × 336 | 384 × 304 |
| | | Scan Time (m:s) | 3:23 | 3:23 | 2:51 | 3:23 | |
| Voxel Volume (mm$^3$) | 1.87 | | | | | | |

TABLE 5

T2W_TSE (5.1.4 - T2 Weighted Fast Spin Echo)

| | Controlled Parameters | Varied Parameters | Series 1/2 | Series 3 | Series 4 | Series 5 | Series 6 |
|---|---|---|---|---|---|---|---|
| Voxel (mm) | 0.55 × 0.71 × 5 | Receive Bandwidth hz/pix | 233.4 | 233.4 | 476.2 | 233.4 | 335.3 |
| Slice Thickness/Gap (mm) | 5/1.2 | Phase Encoding Dir. | RL | AP | RL | RL | RL |
| TE (ms) | 100 | Fat Shift Direction | P | L | P | A | P |
| TR (ms) | 4708 | ETL | 19 | 19 | 19 | 19 | 30 |
| Flip angle (deg) | 90 | Echo Spacing/Shot (ms) | 10/190 | 10/190 | 10/190 | 10/190 | 6.5/194 |
| Whole Body SAR | <4.0 W/kg | Acquisition matrix (pix) | 420 × 323 | 420 × 323 | 420 × 323 | 420 × 323 | 420 × 330 |
| | | Scan Time (m:s) | 2:44 | 2:44 | 4:04 | 2:44 | 3:33 |
| Voxel Volume (mm$^3$) | 1.95 | | | | | | |

TABLE 6

T2W_FLAIR (5.1.5 - FLAIR Sequence)

| | Controlled Parameters | Varied Parameters | Series 1/2 | Series 3 | Series 4 | Series 5 | Series 6 |
|---|---|---|---|---|---|---|---|
| Slice Thickness/Gap (mm) | 5/1.2 | Receive Bandwidth hz/pix | 208.9 | 208.9 | 781.3 | 208.9 | 272.2 |
| TE (ms) | 120 | Phase Encoding Dir. | RL | AP | RL | RL | RL |
| TR (ms) | 6000 | Fat Shift Direction | P | L | P | A | P |
| Inversion Time (ms) | 2000 | ETL | 23 | 23 | 23 | 23 | 36 |
| Whole Body SAR | <2.1 W/kg | Echo Spacing/Shot (ms) | 10/230 | 10/230 | 10/230 | 10/230 | 6.5/233 |
| | | Voxel (mm) | 0.85 × 1.1 × 5 | 0.85 × 1.1 × 5 | 0.9 × 1.28 × 5 | 0.85 × 1.1 × 5 | 0.9 × 1.28 × 5 |
| | | Acquisition matrix (pix) | 272 × 207 | 272 × 207 | 256 × 184 | 272 × 207 | 256 × 180 |
| | | Scan Time (m:s) | 4:00 | 4:00 | 3:36 | 4:00 | 3:36 |
| Voxel Volume (mm$^3$) (MAX) | 5.62 | | | | | | |

FIGS. 3A to 3E show various MRI images of a region of the recipient's head resulting from a series of MRI scans. The scans of these figures correspond to the scans used to generate the images of FIGS. 2A to 2E, except for the fact that the scans used to generate the MRI images of FIGS. 3A to 3E were taken of a patient with a cochlear implant attached to the side of the patient's (recipient's) head. As may be seen in FIGS. 3A to 3E, there is an artifact in each of the MRI images distorting the respective images. In some MRI images, the artifact is very significant (e.g. FIG. 3A). The differences between the degree of distortion/size of the artifact are due to the differences of the characteristics of the sequences and parameters of the MRI machine used to take the scans of the regions of the recipient's head. The images of FIGS. 3A to 3E were obtained using MRI machine parameters corresponding to Series 2 presented in the tables above.

As previously indicated, the presence of an implanted medical device including components having magnetic properties (e.g., ferromagnetic materials), whether the component is, for example, a screw, a cochlear implant, etc., often affects the results of a given scan. Specifically, such an implanted medical device may cause the signal received by receiver coil 420 during a scan to have a dramatic loss of signal vis-à-vis a corresponding received signal if the implanted medical device were absent. The resulting artifact in the images prevents that area from being properly imaged and can obscure diseased tissue, such as, for example, a tumor, thus resulting in that tumor (or other ailment) not being detected.

A number of characteristics of MRI imaging result in effects that can distort or otherwise change the results of an MRI image obtained from a scan. One of these characteristics is a chemical shift in general, and a fat shift in particular. In this regard, due to the different molecular environments of protons, the resonant frequency of protons in water and fat differ by approximately 3.5 ppm (220 Hz at 1.5 T). The detected signal from each voxel of a scan is mapped to a position based on its frequency, under the assumption that all protons contained within it resonate at the same frequency. The lower resonant frequency of fat protons causes such protons to be mapped to a lower frequency pixel during frequency encoding gradient direction. This misregistration may not be noticed in tissues with uniform fat-water content. However, the misregistration may produce artifacts at the borders of tissue with significantly different fat water content. Traditionally, various techniques and signal processing are applied in an attempt to minimize the effect of fat shift, hereinafter collectively referred to as "fat shift signal processing."

According to an exemplary embodiment of the present invention, rather than use the fat shift signal processing to minimize the effect of fat shift as is traditionally done, the fat shift signal processing is used to provide a set of MRI images that overall show a reduced artifact/distortion caused by an implanted medical device. This fat shift signal processing also has an effect on the registration of image artifacts resulting from an implantable medical device. This can be used to obtain images with reduced artifact. For example, two sets of images are generated or otherwise obtained, wherein one set of MRI images is obtained via scans taken with the fat shift set in one direction, and the other set of MRI images is obtained via scans taken with the fat shift in an approximately opposite direction. Accordingly, some embodiments of the present invention utilize MRI machines where a technician/operator may select the direction in which fat shift occurs (sometimes constrained by the direction of the frequency encoding gradient), allowing the appearance and orientation of the artifact to be controlled and/or reduced (including eliminated) in the resulting set of MRI images as will be described in greater detail below.

We note that in the following description "fat shift" should be understood to mean the fat shift setting on the MRI machine which controls the fat shift processing performed by the machine.

FIGS. 4A to 4G show another set of MRI images. The MRI images of FIGS. 4A-4C, 4D and 4G are images obtained by scanning the same regions of the recipient that were scanned to obtain the MRI images of FIGS. 3A-3E, respectively, but the scans used to produce the MRI images of FIGS. 4A to 4G were obtained using an MRI machine having a fat shift setting in the reverse direction to that used to obtain the MRI images of FIGS. 3A to 3E. The images of FIGS. 4A to 4G were obtained using MRI machine parameters corresponding to Series 5 presented in the tables above.

Figure 4A:
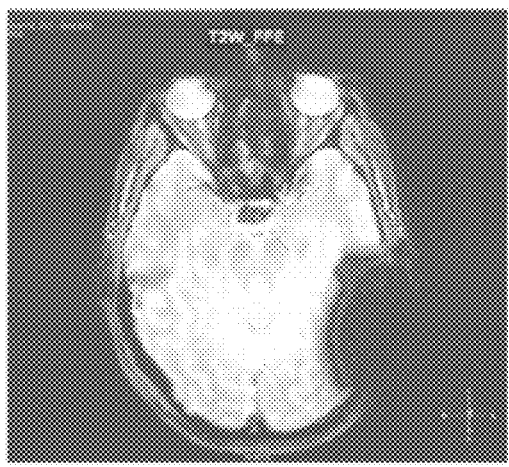
FIG. 4A shows an $8^{th}$ slice of 22 slices of the MRI scan of a recipient with a CI using a T2W_FFE sequence with the fat shift reversed relative to that used to generate the image of FIG. 3A.
Figure 4B:
FIG. 4B shows an $8^{th}$ slice of 22 slices of an MRI scan of a recipient with a CI using a T1W_SE sequence with the fat shift reversed relative to that used to generate the image of FIG. 3B.
Figure 4C:
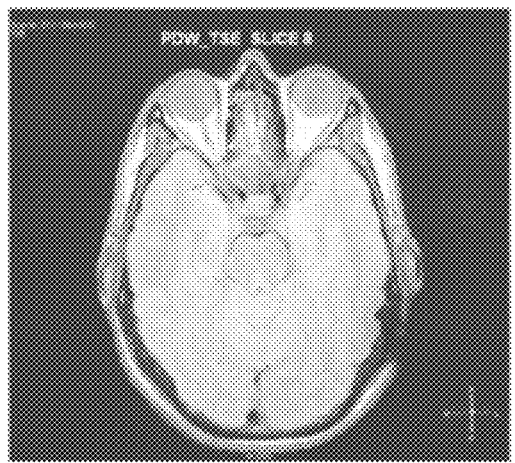
FIG. 4C shows an $8^{th}$ slice of 22 slices of an MRI scan of a recipient with a CI using a PDW-TSE sequence with the fat shift reversed relative to that used to generate the image of FIG. 3C.
Figure 4D:
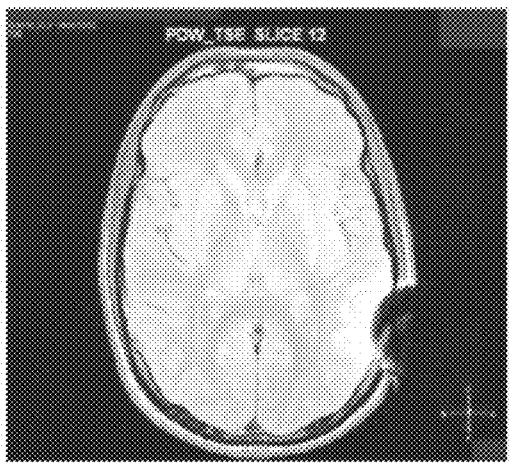
FIG. 4D shows a $12^{th}$ slice of 22 slices of an MRI scan of a recipient with a CI using a PDW-TSE sequence with the fat shift reversed relative to that used to generate the image of FIG. 3C.

With respect to FIGS. 4C and 4D, it may be seen that FIG. 4C shows an MRI image taken with a scan at a region of the recipient's head identified as slice 8 and that FIG. 4D shows an MRI image taken with a scan at a region of the recipient's head identified as slice 12, slice 12 corresponding to a slice of the recipient's head a distance from slice 8.

Figure 3A:
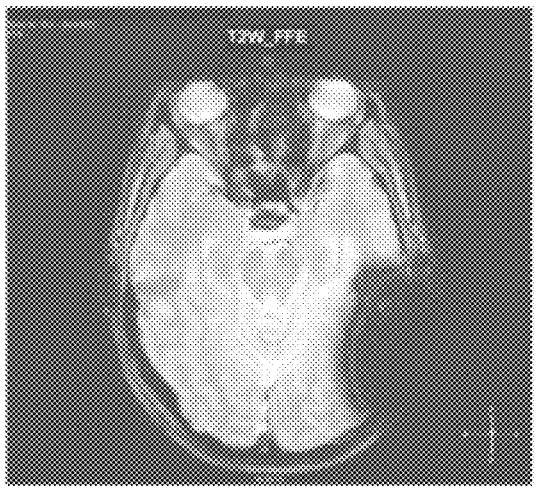
FIG. 3A shows an $8^{th}$ slice of 22 slices of an MRI scan of a recipient with a CI using a T2W_FFE sequence.
Figure 3B:
FIG. 3B shows an $8^{th}$ slice of 22 slices of an MRI scan of a recipient with a CI using a T1W_SE sequence.
Figure 3C:
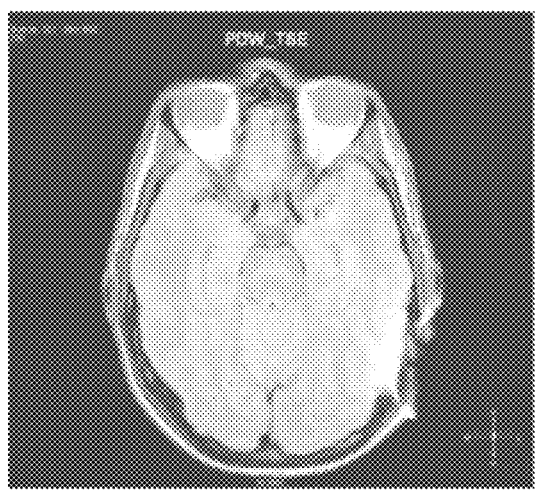
FIG. 3C shows an $8^{th}$ slice of 22 slices of an MRI scan of a recipient with a CI using a PDW-TSE sequence.

Comparing FIG. 4C to FIG. 3C (FIG. 3 C showing an MRI image obtained at slice 8, except obtained with a scan using MRI machine parameters corresponding to Series 2 of the above charts, as detailed above), it may be seen that the artifact of FIG. 3C and the artifact of FIG. 4C is different. Specifically, the artifact appears far less pronounced in FIG. 4C than in FIG. 3C. The only substantive difference between these two images is that the fat shift setting for the scan used to obtain the MRI image of FIG. 4C has been reversed from P (posterior) to A (anterior) directions (see Table 4 above) relative to the scan used to obtain the MRI image of FIG. 3C. All other substantive parameter settings of the MRI machine are the same when scanning to obtain these images.

With respect to FIG. 4D, which shows an MRI image taken at slice 12 instead of slice 8 of the recipient, the artifact appears more pronounced with respect to the MRI image of FIG. 4C, and the distortion effects are more analogous to those of FIG. 3C than to those of FIG. 4C. This is due to the effect of reversing the fat shift direction of the scans used to produce the MRI images of FIGS. 4A-4G, which effectively shifts the location of the artifact "upwards" from slice 8 to slice 12 of the recipient. It is noted that in other embodiments, a useful effect may be obtained by shifting the location of the artifact "downward."

Figure 3D:
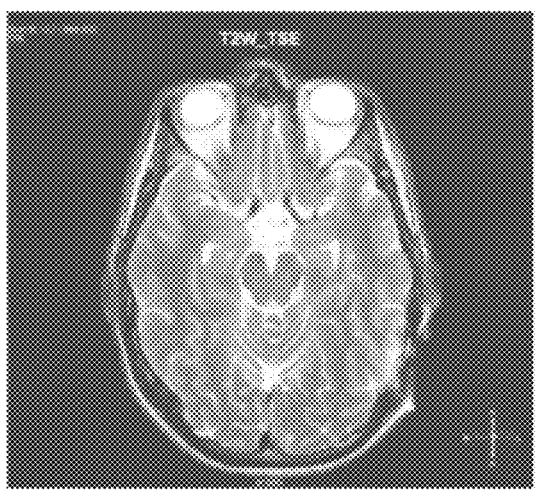
FIG. 3D shows an $8^{th}$ slice of 22 slices of an MRI scan of a recipient with a CI using a T2W-TSE sequence.
Figure 3E:
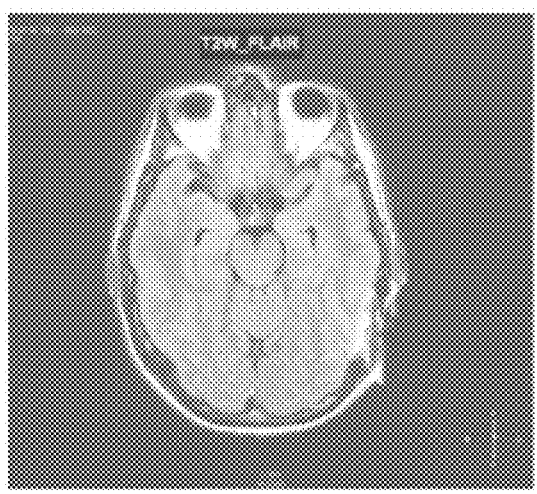
FIG. 3E shows an $8^{th}$ slice of 22 slices of an MRI scan of a recipient with a CI using a T2W_FLAIR sequence.
Figure 4E:
FIG. 4E shows an $8^{th}$ slice of 22 slices of an MRI scan of a recipient with a CI using a T2W-TSE sequence with the fat shift reversed relative to that used to generate the image of FIG. 3D.
Figure 4F:
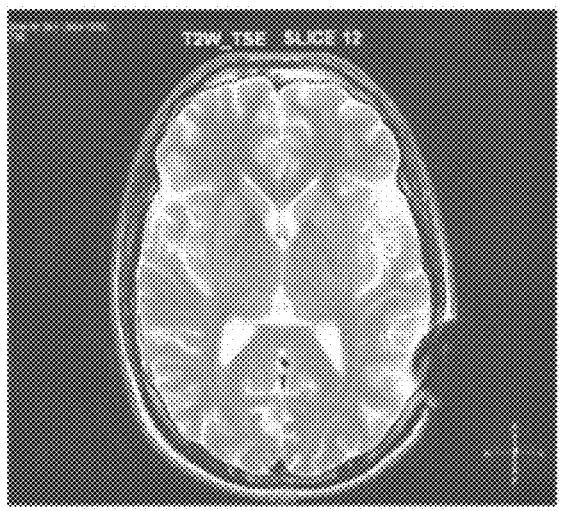
FIG. 4F shows a $12^{th}$ slice of 22 slices of an MRI scan of a recipient with a CI using a T2W-TSE sequence with the fat shift reversed relative to that used to generate the image of FIG. 3D.
Figure 4G:
FIG. 4G shows an $8^{th}$ slice of 22 slices of an MRI scan of a recipient with a CI using a T2W_FLAIR sequence with the fat shift reversed relative to that used to generate the image of FIG. 3E.

FIGS. 4E and 4F present another example of this effect. FIGS. 4E and 3D are MRI image obtained at slice 8, except that the image of FIG. 4E is obtained with a scan using MRI machine parameters corresponding to Series 5, and the image of FIG. 3D is obtained with a scan using MRI machine parameters corresponding to Series 2, both obtained using a T2W_TSE sequence, but with the fat shift direction reversed from P (posterior) to A (anterior) directions (see Table 5) for the scan used to obtain the MRI image of FIG. 4E. Again, it may be seen that the artifact in FIG. 4E is different (less pronounced/distorting) when compared to that of FIG. 3D, both showing an MRI image obtained at slice 8. FIG. 4F however, showing an MRI image obtained at slice 12, has a more pronounced (more distorting) artifact than that shown in FIG. 4E. Again, this is because the artifact has effectively been shifted a number of slices between the scan sequence used to obtain the MRI image of FIG. 3D and that of FIGS. 4E and 4F, due to the change in direction of the fat shift setting.

Accordingly, amongst the collection of MRI images of the two sets of MRI images presented in FIGS. 3A-3E and 4A-4G, there are images of slice 8 with reduced (little to no) artifact, and images of slice 8 with some or even an increased artifact. Embodiments of the present invention include selecting MRI images from each MRI image set that have a reduced/eliminated artifact to provide a full set of MRI images with reduced artifact/distortion when compared to a set of MRI images of a given slice of the recipient using the same fat shift setting.

In view of the above, in an exemplary embodiment of the present invention, a set of MRI images with a reduced artifact may be obtained by generating or otherwise obtaining, a first set of MRI images of the recipient using a first fat shift direction, generating or otherwise obtaining a second set of MRI images of the recipient using a second fat shift direction, approximately opposite to the first fat shift direction, and producing a new set of MRI images by selecting a sub-set of MRI images from the first set and a sub-set of images from the second set such that the artifact present in the MRI images in the produced set of MRI images is reduced for one or more MRI images of the set of MRI images when compared to the artifact in either of the first and second sets.

Figure 5A:
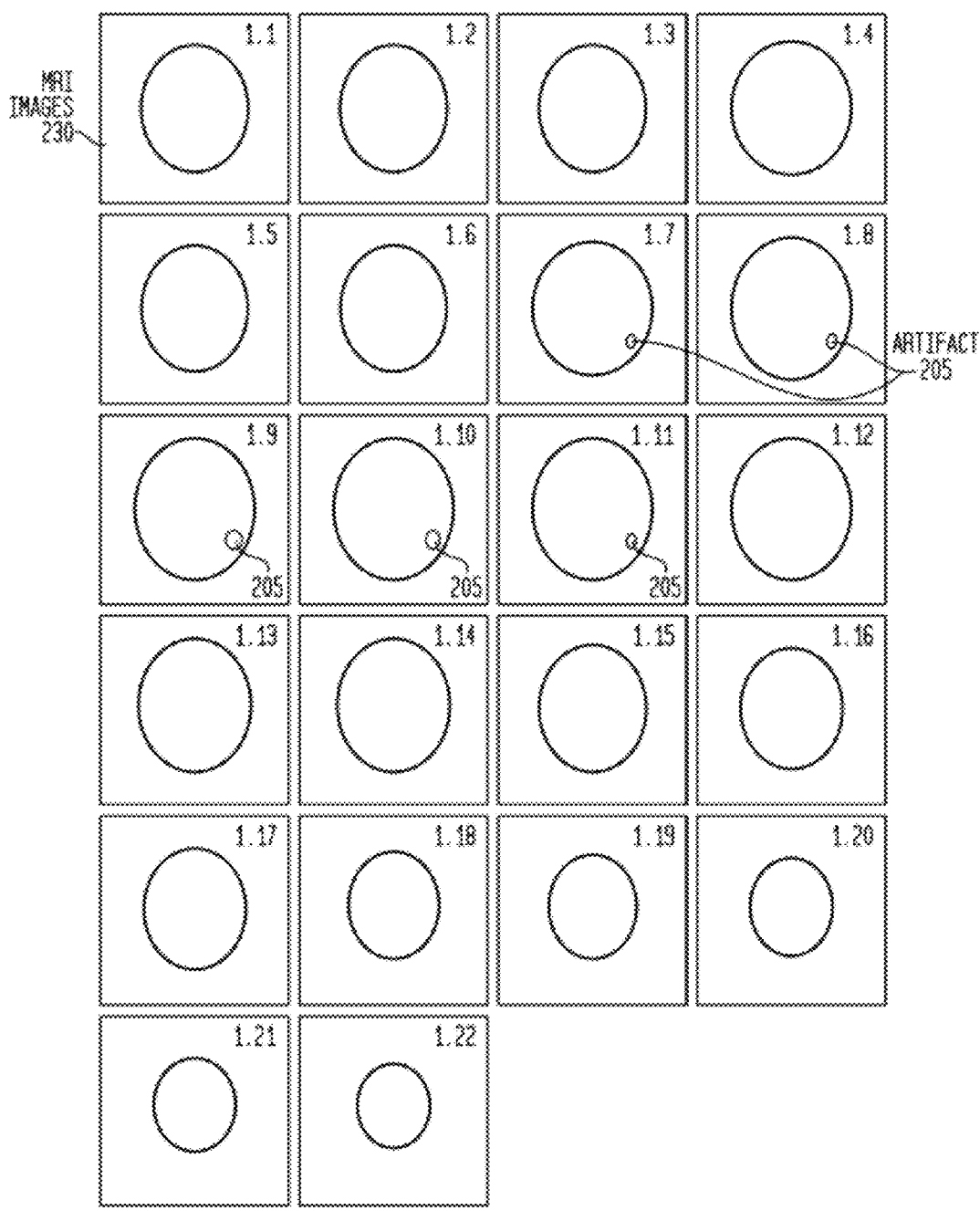
FIG. 5A shows a representative first set of MRI images.
Figure 5B:
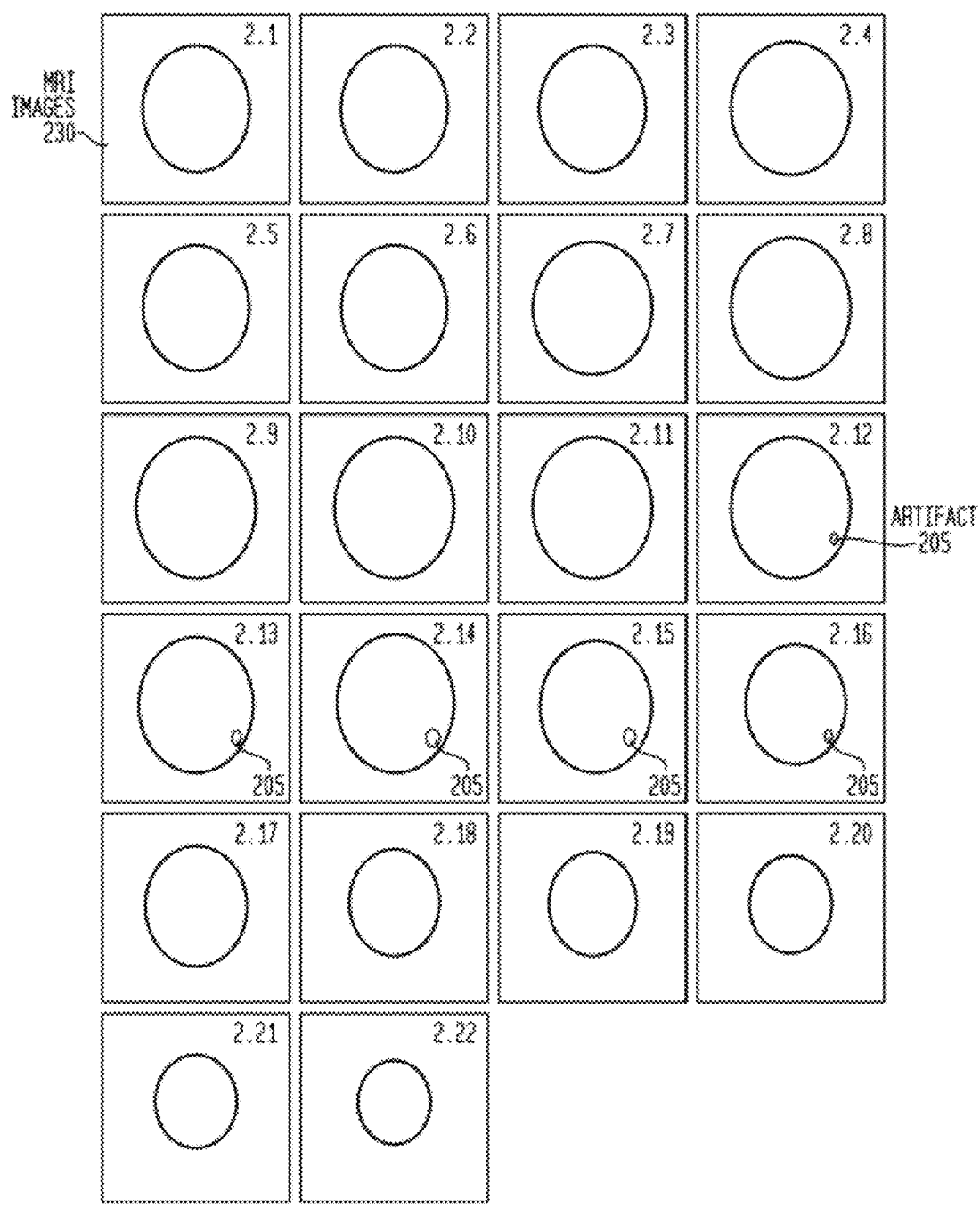
FIG. 5B shows a representative second set of MRI images.
Figure 5C:
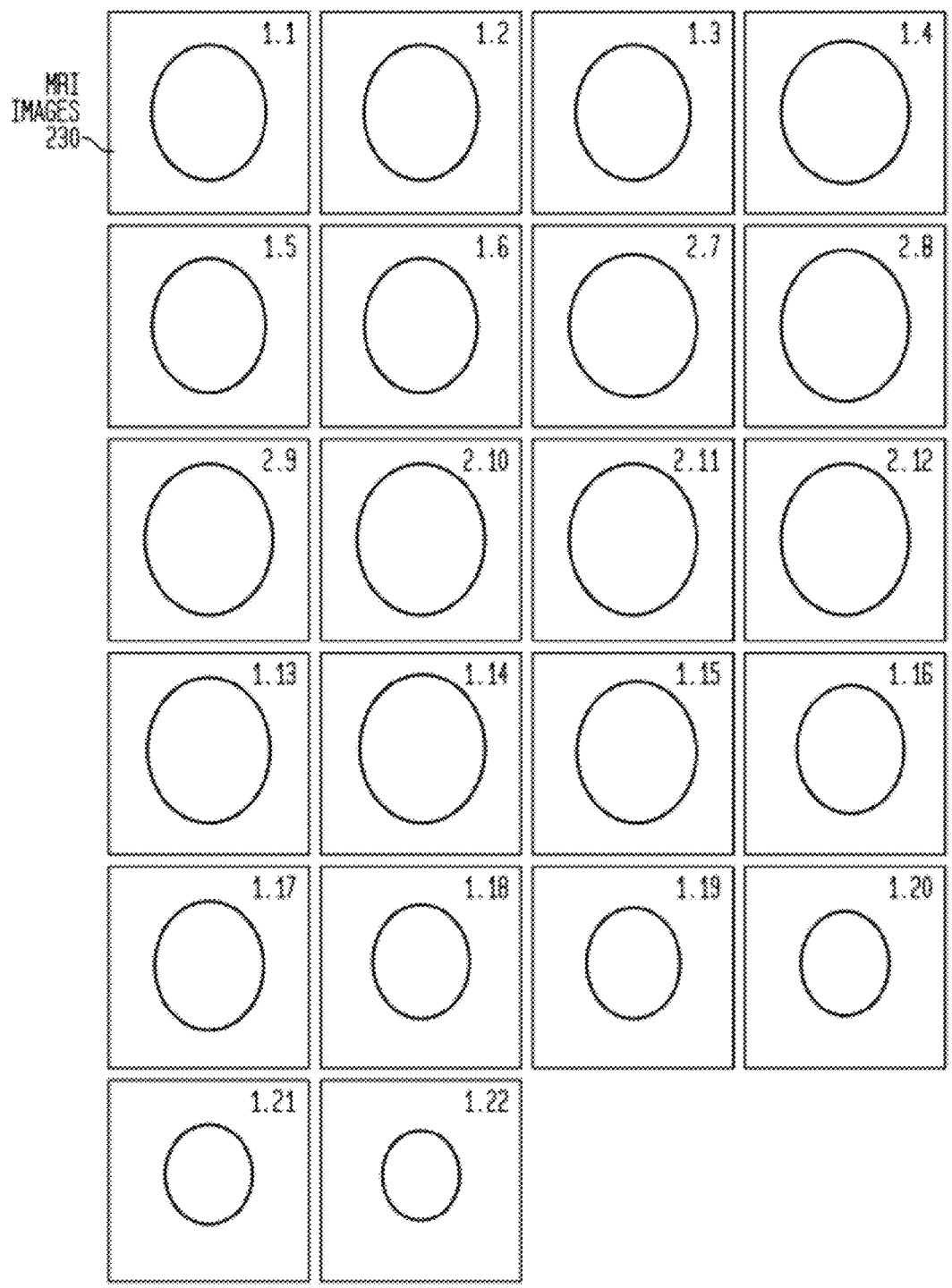
FIG. 5C shows a representative generated set of MRI images obtained according to an embodiment of the present invention.

An exemplary method of producing a new set of MRI images will now be discussed with reference to FIGS. 5A, 5B and 5C. FIGS. 5A-5C illustrate representative images 230 of three different MRI image set I (210) MRI image set II (220) and MRI image set III (200), respectively. FIG. 5A schematically illustrates the first set 210 (MRI image set I) of MRI images 230, comprising in this case, 22 MRI images labeled 1.1, 1.2, 1.3, 1.4, 1.5, 1.6, 1.7, 1.8, 1.9, 1.10, 1.11, 1.12, 1.13, 1.14, 1.15, 1.16, 1.17, 1.18, 1.19, 1.20, 1.21 and 1.22. Each of these MRI images 230 corresponds to an MRI image resulting from a scan of a given slice of a region of the recipient's head (22 slices in total), each a known and acceptable distance from the other.

MRI images 1.7, 1.8, 1.9, 1.10 and 1.11 show an artifact 205 indicated representatively as an oval. The artifact 205 appears first in MRI image 1.7 and grows in 1.8 and 1.9 and then begins to decrease images 1.10 and 1.11 and by image 1.12, it has disappeared. All other MRI images of the set depicted in FIG. 5A show no sign of the artifact 205.

FIG. 5B shows a second set 220 (MRI image set II) of MRI images 230, comprising in this case, 22 MRI images 2.1, 2.2, 2.3, 2.4, 2.5, 2.6, 2.7, 2.8, 2.9, 2.10, 2.11, 2.12, 2.13, 2.14, 2.15, 2.16, 2.17, 2.18, 2.19, 2.20, 2.21 and 2.22. Each of these images 230 corresponds to an slice of the MRI image taken of the recipient an MRI image resulting from a scan of a given slice of a region of the recipient's head (22 slices in total), each an acceptable known distance from the other, obtained in the same manner as those of FIG. 5A save for the fact that the direction of the fat shift setting has been reversed.

In this second set 220 (MRI image set II) of images 230, MRI images 2.7 to 2.11 (corresponding to the same slices of the recipient from which MRI images 1.7 to 1.11 of FIG. 5A were obtained) show no sign of the artifact 205, in contrast to the corresponding MRI images of FIG. 5A. However, with the fat shift direction reversed, the artifact 205 has effectively been shifted upwards by 5 slices, to appear in MRI images 2.12, 2.13, 2.14, 2.15 and 2.16, and disappearing again from MRI images 2.17 and onwards.

In the exemplary method now being described, a subset of MRI images from the first set 210 (MRI image set I) of MRI images 230 is selected, which have little or no or at least reduced artifact when compared with the corresponding MRI image 230 of second set 220 (MRI image set II), and a sub-set 221 of second set 220 (MRI image set II) of MRI images 230 is selected which have little or no or reduced artifact when compared with the corresponding MRI image 230 of first set 210 (MRI image set I). Accordingly, the result of the exemplary method is such that the sub-set of first set 210 (MRI image set I) comprises images 1.1, 1.2, 1.3, 1.4, 1.5, 1.6, 1.12, 1.13, 1.14, 1.15, 1.16, 1.17, 1.18, 1.19, 1.20, 1.21 and 1.22, and the sub-set 221 of second set 220 (MRI image set II) comprises images 2.1, 2.2, 2.3, 2.4, 2.5, 2.6, 2.7, 2.8, 2.9, 2.10, 2.11, 2.17, 2.18, 2.19, 2.20, 2.21 and 2.22.

The images from these sub-sets are combined to form a new set 200 (MRI image set III) of MRI images, represented by MRI images 230 shown in FIG. 5C, with little or no or reduced artifact in those images vis-à-vis the corresponding images of the sets depicted in FIG. 5A and FIG. 5B. FIG. 5C shows the set 200 (MRI image set III) of MRI images 230 comprising images 1.1, 1.2, 1.3, 1.4, 1.5, 1.6, 2.7, 2.8, 2.9, 2.10, 2.11, 1.12, 1.13, 1.14, 1.15, 1.16, 1.17, 1.18, 1.19, 1.20, 1.21 and 1.22. It will be appreciated that other combinations of sub-sets may also be selected to form a new set of MRI images, such as by way of example only, 2.1, 2.2, 2.3, 2.4, 2.5, 2.6, 2.7, 2.8, 2.9, 2.10, 2.11, 1.12, 1.13, 1.14, 1.15, 1.16, 1.17, 1.18, 1.19, 1.20, 1.21 and 1.22; or 1.1, 1.2, 1.3, 1.4, 1.5, 1.6, 2.7, 2.8, 2.9, 2.10, 2.11, 1.12, 1.13, 1.14, 1.15, 1.16, 2.17, 2.18, 2.19, 2.20, 2.21 and 2.22.

According to the exemplary method now being described, for each of the 22 slices of the recipient, the corresponding MRI image with the larger artifact has been omitted, and the corresponding MRI image with the smaller artifact has been selected.

In some embodiments, the first set 210 (MRI image set I) of MRI images and the second set 220 (MRI image set II) of MRI images may not have exactly the same number of MRI images 230 as each other. For example the first set 210 (MRI image set I) may have 18 images and the second set 220 (MRI image set II) may have 20 images. Any size set will suffice providing that the present invention may be practiced.

Some embodiments of the present invention include methods in which the MRI image with an artifact is not excluded. In such a method, at least one MRI image with an artifact smaller than that of a corresponding MRI image (or near corresponding MRI image in the case where the image numbers are not equal in both sets) is selected in place of the corresponding MRI image, the produced improved set of MRI images having an overall reduced artifact when compared with either of the first set 210 (MRI image set I) or the second set 220 (MRI image set II) of MRI images.

Figure 6A:
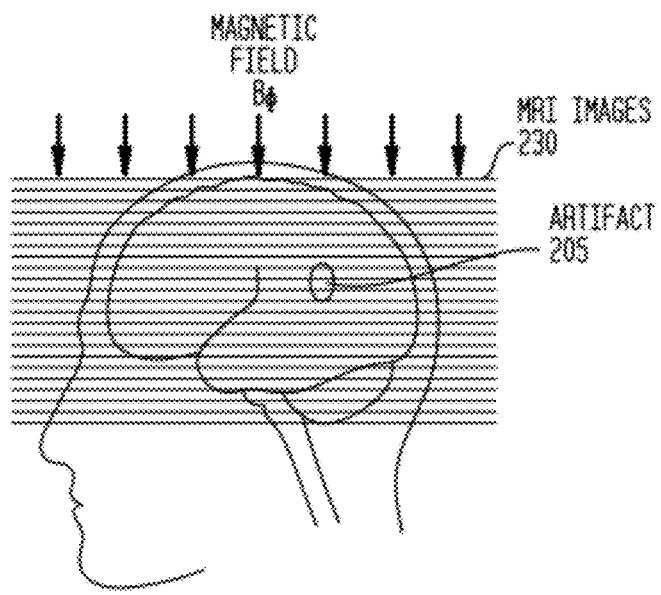
FIG. 6A shows a side profile of the recipient produced by transposing the results of the MRI images of FIG. 5A, where the MRI scan slices shown interposed through the head of the recipient.

FIG. 6A schematically shows a side profile of the recipient 50 produced by transposing the results of the MRI images of FIG. 5A, the MRI scan slices shown interposed through the head of the recipient 50. The artifact 205 appears in the side location of slices 7 to 11 because the artifact appears in the MRI image for those slices, as is shown in FIG. 5A. FIG. 6A also shows the direction of the magnetic field $B_\Phi$.

Figure 6B:
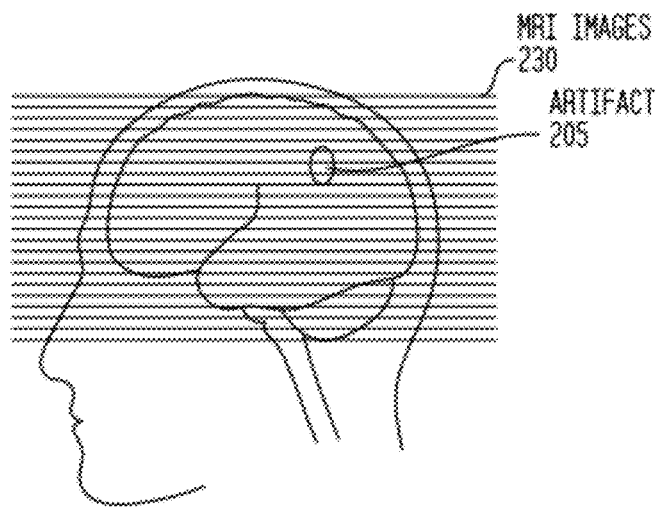
FIG. 6B shows a side profile of the recipient produced by transposing the results of the MRI images of FIG. 5B, where the MRI scan slices shown interposed through the head of the recipient.

FIG. 6B schematically shows a side profile of the recipient 50 produced by transposing the results of the MRI images of FIG. 5B, the MRI scan slices again shown interposed through the head of the recipient 50. In generating this set of images, the fat shift direction has been reversed relative to that used to develop the profile depicted in FIG. 6A. The artifact 205 appears shifted "upwards" as shown in FIG. 6B, and appears in the slices corresponding to slides 2.12 to 2.16 of FIG. 5B.

In some embodiments of the present invention, the artifact may move "upwards" or "downwards" in the side profiles by about 25 mm. This is roughly equivalent to the average radius of artifacts produced by typical cochlear implants.

Figure 6C:
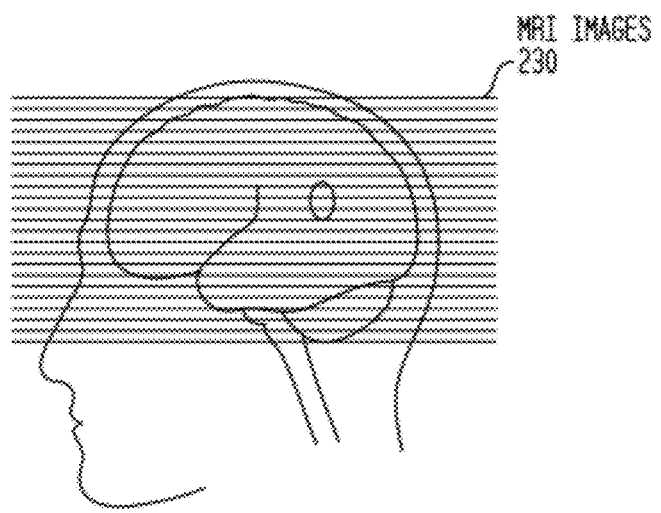
FIG. 6C shows a side profile of the recipient produced by transposing the results of the MRI images of FIG. 5C, where the MRI scan slices shown interposed through the head of the recipient.

FIG. 6C schematically shows a side profile of the recipient 50 produced by transposing the results of the MRI images of FIG. 5C, the MRI scan slices again shown interposed through the head of the recipient 50. In this combined set, the artifact 205 has been eliminated to provide a side profile with a reduced or eliminated artifact.

Figure 7:
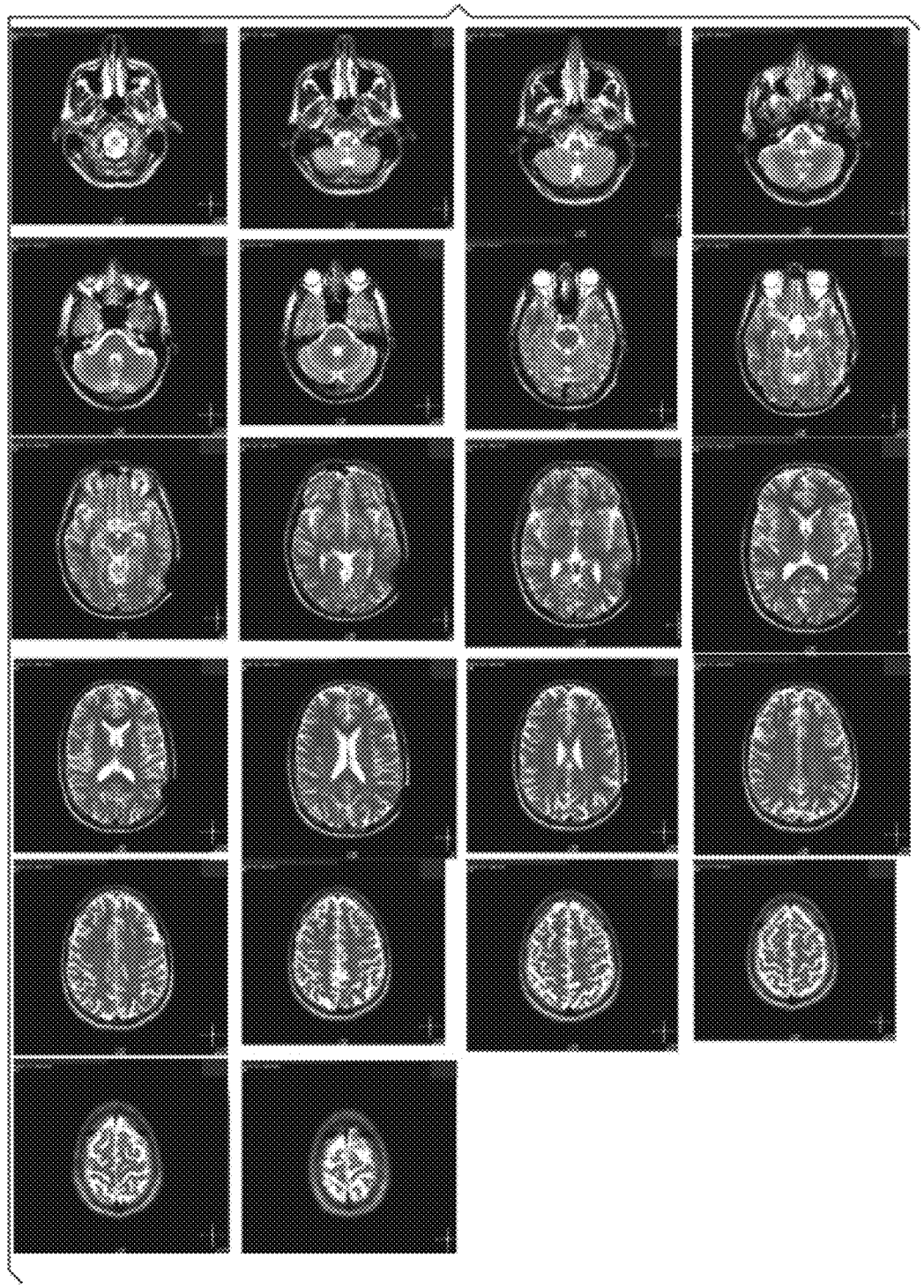
FIG. 7 shows slices 1-22 respectively, of an MRI scan of a recipient with a CI using a T2W_TSE sequence.
Figure 8:
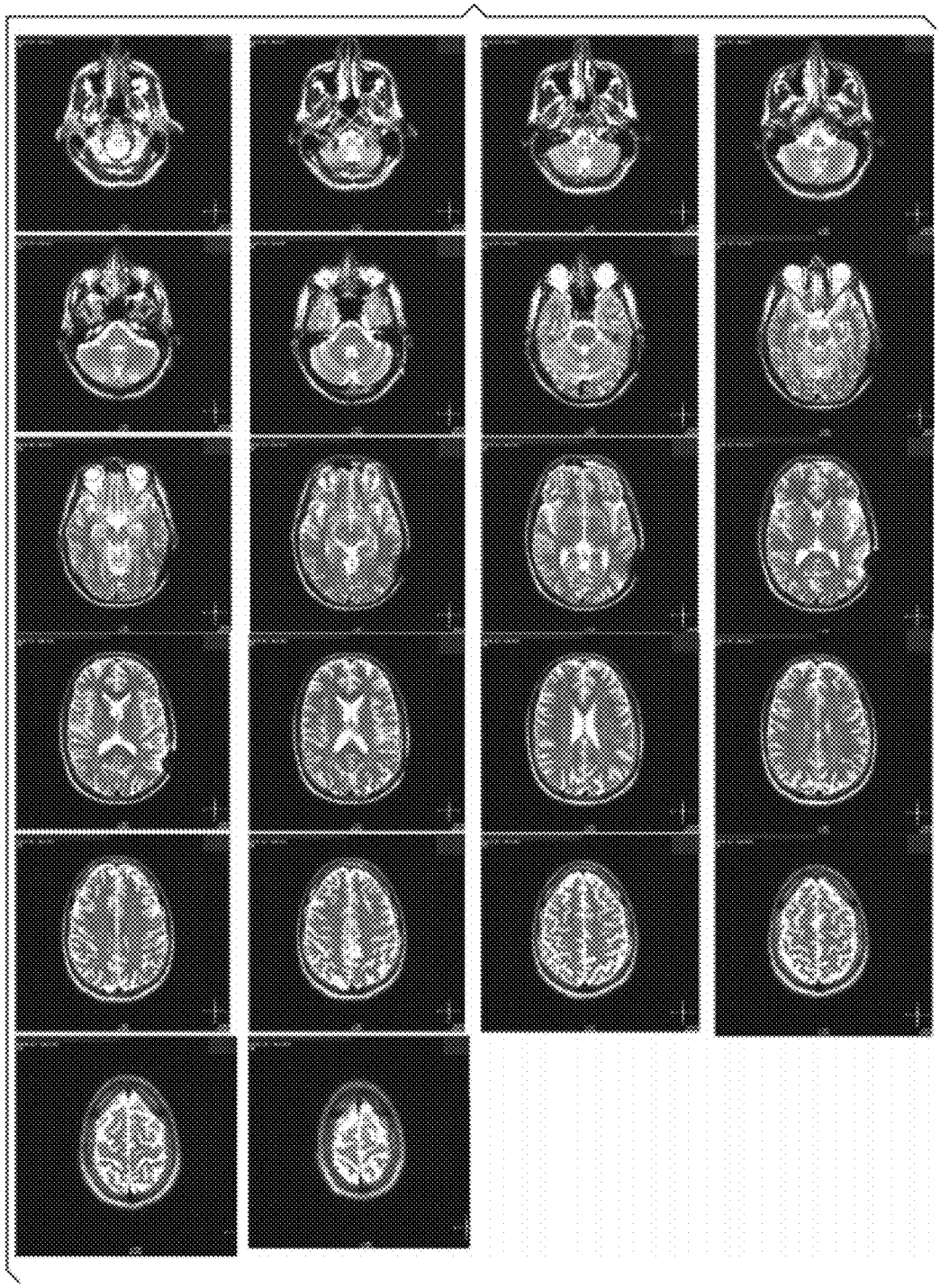
FIG. 8 show slices 1-22 of an MRI scan of a recipient with a CI using a T2W_TSE sequence with the fat shift reversed relative to that used to generate the images of FIG. 7.
Figure 9:
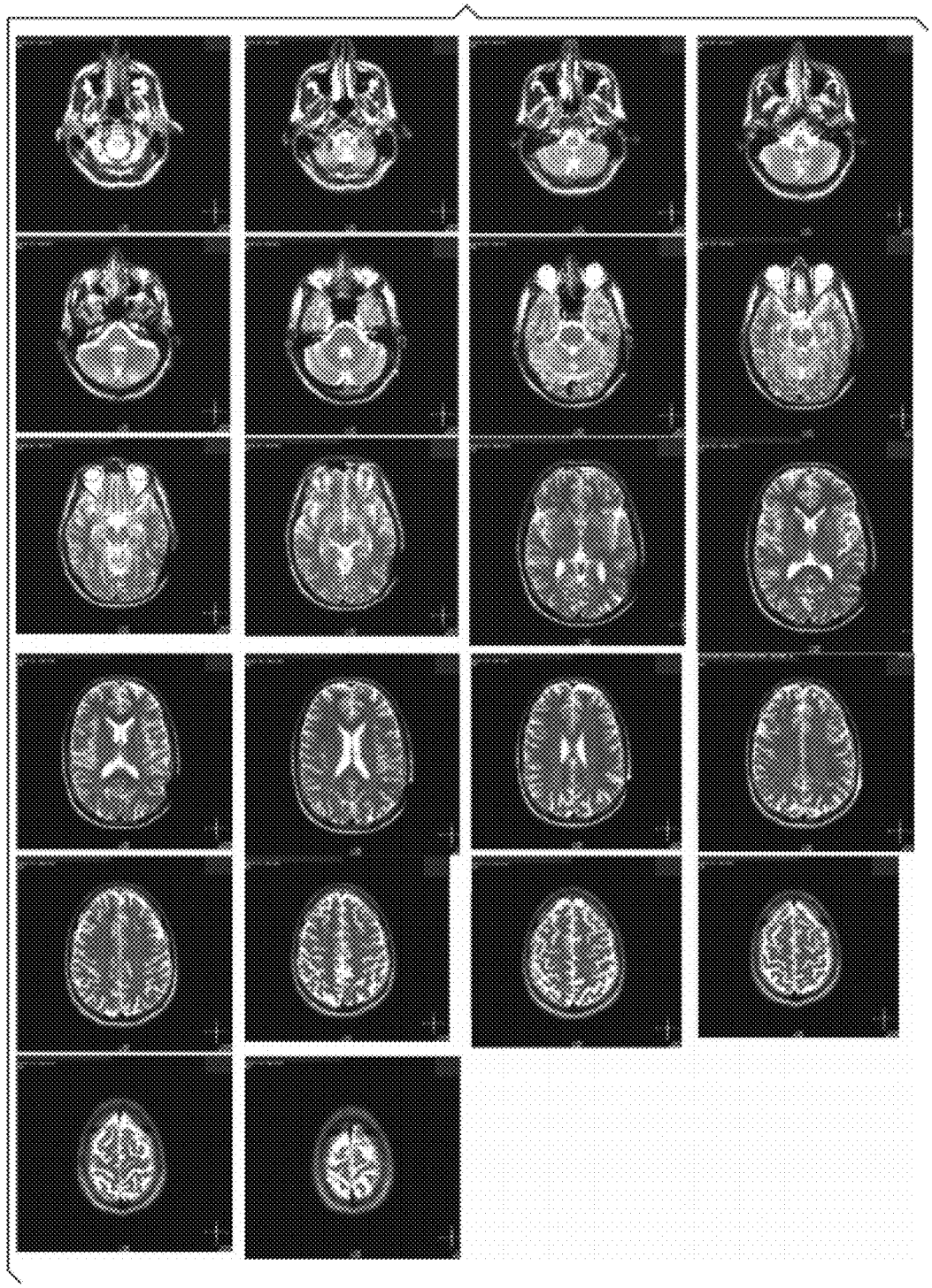
FIG. 9 shows slices 1-22 of a combined set of slices from FIGS. 7 and 8 obtained according to an embodiment of the present invention.

FIGS. 7-9 further illustrate an exemplary method of the present invention. In such a method, MRI scans are taken of 22 different slices of a recipient having a cochlear implant implanted in the recipient's head using a T2W_TSE sequence. This produces the MRI images shown in FIG. 7, thereby producing a first set of MRI images. As may be seen from the MRI images of FIG. 7, the MRI images corresponding to slices 8, 9 and 10 (slice 1 being at the top left, slice 22 being at the bottom right) show signs of an artifact resulting from the implanted cochlear implant.

The detailed listing of the protocol settings that may be used for this fast spin echo sequence follows, as would readily be understood by one of ordinary skill in the art:

The scans are transverse (axial) slices.

The voxel volume is <3 mm$^3$.

Fast Spin Echo (T2 Weighting)

TE≈100

TR≈4000 ms

ETL≈20 (inter echo spacing to be minimized)

The MRI machine used was a Philips Intera 1.5 T MRI scanner.

| Philips Intera technical parameters | |
| --- | --- |
| Main Field Strength (T) | 1.5 |
| Main Field Inhomogeneities (ppm) | <0.27 |
| Maximum gradient amplitude (mT m$^{-1}$) | 33 |
| Gradient slew rate (mT m$^{-1}$ ms$^{-1}$) | 80 |

| T2W_TSE | |
|---|---|
| Coil selection = | "SENSE-Head-8"; |
| element selection = | "SENSE"; |
| connection = | "d"; |
| Dual coil = | "no"; |
| Homogeneity correction = | "none"; |
| CLEAR = | "yes"; |
| FOV  AP (mm) = | 230; |
|      RL (mm) = | 230; |
|      FH (mm) = | 135.199997; |
| Voxel size  AP (mm) = | 0.550000012; |
|             RL (mm) = | 0.684523821; |
| Slice thickness (mm) = | 5; |
| Recon voxel size (mm) = | 0.224609375; |
| Fold-over suppression = | "no"; |
| Reconstruction matrix = | 1024; |
| SENSE = | "no"; |
| Stacks = | 1; |
| type = | "parallel"; |
| slices = | 22; |
| slice gap = | "recipient defined"; |
| gap (mm) = | 1.19999981; |
| slice orientation = | "transverse"; |
| fold-over direction = | "RL"; |
| fat shift direction = | "P"; |
| Stack Offc.  AP (P = +mm) = | 0; |
|              RL (L = +mm) = | 0; |
|              FH (H = +mm) = | 0; |
| Ang.  AP (deg) = | 0; |
|       RL (deg) = | 0; |
|       FH (deg) = | 0; |
| Minimum number of packages = | 1; |
| Slice scan order = | "default"; |
| Large table movement = | "no"; |
| PlanAlign = | "no"; |
| REST slabs = | 0; |
| Recipient position = | "head first"; |
| orientation = | "supine"; |
| scan mode = | "MS"; |
| technique = | "SE"; |
| Modified SE = | "no"; |
| Acquisition mode = | "cartesian"; |
| Fast imaging mode = | "TSE"; |
| shot mode = | "multishot"; |
| TSE factor = | 19; |
| start up echoes = | 0; |
| profile order = | "linear"; |
| DRIVE = | "no"; |
| ultrashort = | "no"; |
| Echoes = | 1; |
| partial echo = | "no"; |
| TE = | "recipient defined"; |
| (ms) = | "100"; |
| Flip angle (deg) = | 90; |
| Refocusing control = | "no"; |
| TR = | "shortest"; |
| Halfscan = | "no"; |
| Water-fat shift = | "maximum"; |
| Shim = | "default"; |
| Fat suppression = | "no"; |
| Water supression = | "no"; |
| BB pulse = | "no"; |
| MTC = | "no"; |
| Diffusion mode = | "no"; |
| SAR mode = | "high"; |
| B1 mode = | "default"; |
| PNS mode = | "low"; |
| Gradient mode = | "default"; |
| SoftTone mode = | "no"; |
| Cardiac synchronization = | "no"; |
| Respiratory compensation = | "no"; |
| Flow compensation = | "no"; |
| Motion smoothing = | "yes"; |
| NSA = | 2; |
| SMART = | "yes"; |
| Manual start = | "no"; |
| Dynamic study = | "no"; |
| Preparation phases = | "auto"; |
| Manual Offset Freq. = | "no"; |
| MIP/MPR = | "no"; |
| Images = | "M", (3) "no"; |
| Autoview image = | "M"; |
| Calculated images = | (4) "no"; |
| Reference tissue = | "white matter"; |
| Preset window contrast = | "soft"; |
| Reconstruction mode = | "immediate"; |
| Save raw data = | "no"; |
| Hardcopy protocol = | "no"; |
| Ringing filtering = | "default"; |
| Geometry correction = | "default"; |
| IF_info_seperator = | 1634755923; |
| Total scan duration = | "02:44:8"; |
| Rel. signal level (%) = | 100; |
| Act. TR (ms) = | "4708"; |
| Act. TE (ms) = | "100"; |
| ACQ matrix M × P = | "420 × 323"; |
| ACQ voxel MPS (mm) = | "0.55/0.71/5.00"; |
| REC voxel MPS (mm) = | "0.22/0.22/5.00"; |
| Scan percentage (%) = | 76.9047623; |
| Packages = | 1; |
| Min. slice gap (mm) = | 0; |
| WFS (pix)/BW (Hz) = | "0.981/221.5"; |
| TSE es/shot (ms) = | "10.0/190"; |
| SAR/whole body = | "<100%/4.0 W/kg"; |
| Whole body/level = | "<4.0 W/kg/$1^{st}$ level"; |
| B1 rms [uT]= | 4.53137493; |
| PNS/level = | "37%/normal"; |
| Sound Pressure Level (dB) = | 8.32736969; |

Next, MRI scans are taken of the same 22 slices of the recipient 50 used to generate the MRI images of FIG. 7, again using a T2W_TSE sequence. This produces the MRI images shown in FIG. 8, thereby producing a second set of MRI images. As may be seen from the MRI images of FIG. 8, the MRI images corresponding to slices 11, 12 and 13 (slice 1 being at the top left, slice 22 being at the bottom right) show significant signs of an artifact resulting from the implanted cochlear implant.

The detailed listing of the protocol settings is identical to those used above but with the fat shift direction set to A instead of P as follows, as would readily be understood by one of ordinary skill in the art:

| Coil selection = | "SENSE-Head-8"; |
|---|---|
| element selection = | "SENSE"; |
| connection = | "d"; |
| Dual coil = | "no"; |
| Homogeneity correction = | "none"; |
| CLEAR = | "yes"; |
| FOV  AP (mm) = | 230; |
|      RL (mm) = | 230; |
|      FH (mm) = | 135.199997; |
| Voxel size  AP (mm) = | 0.550000012; |
|             RL (mm) = | 0.684523821; |
| Slice thickness (mm) = | 5; |
| Recon voxel size (mm) = | 0.224609375; |
| Fold-over suppression = | "no"; |
| Reconstruction matrix = | 1024; |
| SENSE = | "no"; |
| Stacks = | 1; |
| type = | "parallel"; |
| slices = | 22; |
| slice gap = | "recipient defined"; |
| gap (mm) = | 1.19999981; |
| slice orientation = | "transverse"; |
| fold-over direction = | "RL"; |
| fat shift direction = | "A"; |
| Stack Offc.  AP (P = +mm) = | 0; |
|              RL (L = +mm) = | 0; |
|              FH (H = +mm) = | 0; |
| Ang.  AP (deg) = | 0; |
|       RL (deg) = | 0; |
|       FH (deg) = | 0; |

-continued

| | |
|---|---|
| Minimum number of packages = | 1; |
| Slice scan order = | "default"; |
| Large table movement = | "no"; |
| PlanAlign = | "no"; |
| REST slabs = | 0; |
| Recipient position = | "head first"; |
| orientation = | "supine"; |
| scan mode = | "MS"; |
| technique = | "SE"; |
| Modified SE = | "no"; |
| Acquisition mode = | "cartesian"; |
| Fast imaging mode = | "TSE"; |
| shot mode = | "multishot"; |
| TSE factor = | 19; |
| start up echoes = | 0; |
| profile order = | "linear"; |
| DRIVE = | "no"; |
| ultrashort = | "no"; |
| Echoes = | 1; |
| partial echo = | "no"; |
| TE = | "recipient defined"; |
| (ms) = | "100"; |
| Flip angle (deg) = | 90; |
| Refocusing control = | "no"; |
| TR = | "shortest"; |
| Halfscan = | "no"; |
| Water-fat shift = | "maximum"; |
| Shim = | "default"; |
| Fat suppression = | "no"; |
| Water supression = | "no"; |
| BB pulse = | "no"; |
| MTC = | "no"; |
| Diffusion mode = | "no"; |
| SAR mode = | "high"; |
| B1 mode = | "default"; |
| PNS mode = | "low"; |
| Gradient mode = | "default"; |
| SoftTone mode = | "no"; |
| Cardiac synchronization = | "no"; |
| Respiratory compensation = | "no"; |
| Flow compensation = | "no"; |
| Motion smoothing = | "yes"; |
| NSA = | 2; |
| SMART = | "yes"; |
| Manual start = | "no"; |
| Dynamic study = | "no"; |
| Preparation phases = | "auto"; |
| Manual Offset Freq. = | "no"; |
| MIP/MPR = | "no"; |
| Images = | "M", (3) "no"; |
| Autoview image = | "M"; |
| Calculated images = | (4) "no"; |
| Reference tissue = | "white matter"; |
| Preset window contrast = | "soft"; |
| Reconstruction mode = | "immediate"; |
| Save raw data = | "no"; |
| Hardcopy protocol = | "no"; |
| Ringing filtering = | "default"; |
| Geometry correction = | "default"; |
| IF_info_seperator = | 1634755923; |
| Total scan duration = | "02:44:8"; |
| Rel. signal level (%) = | 100; |
| Act. TR (ms) = | "4708"; |
| Act. TE (ms) = | "100"; |
| ACQ matrix M × P = | "420 × 323"; |
| ACQ voxel MPS (mm) = | "0.55/0.71/5.00"; |
| REC voxel MPS (mm) = | "0.22/0.22/5.00"; |
| Scan percentage (%) = | 76.9047623; |
| Packages = | 1; |
| Min. slice gap (mm) = | 0; |
| WFS (pix)/BW (Hz) = | "0.981/221.5"; |
| TSE es/shot (ms) = | "10.0/190"; |
| SAR/whole body = | "<100%/4.0 W/kg"; |
| Whole body/level = | "<4.0 W/kg/1$^{st}$ level"; |
| B1 rms [uT]= | 4.53137493; |
| PNS/level = | "37%/normal"; |
| Sound Pressure Level (dB) = | 8.32736969; |

FIG. 9 show a set of improved MRI images for slices 1—obtained by combining MRI images from the set of FIG. 7 with MRI images from the set of FIG. 8. This set of improved MRI images is generated by combining selected MRI images from the set of FIG. 7 and the set of FIG. 8. It may be seen that the MRI images of the improved set of MRI images presented in FIG. 9 have no or at least reduced artifact as compared to the MRI images of the respective slices of the sets of FIGS. 7 and 8.

Figure 10A:
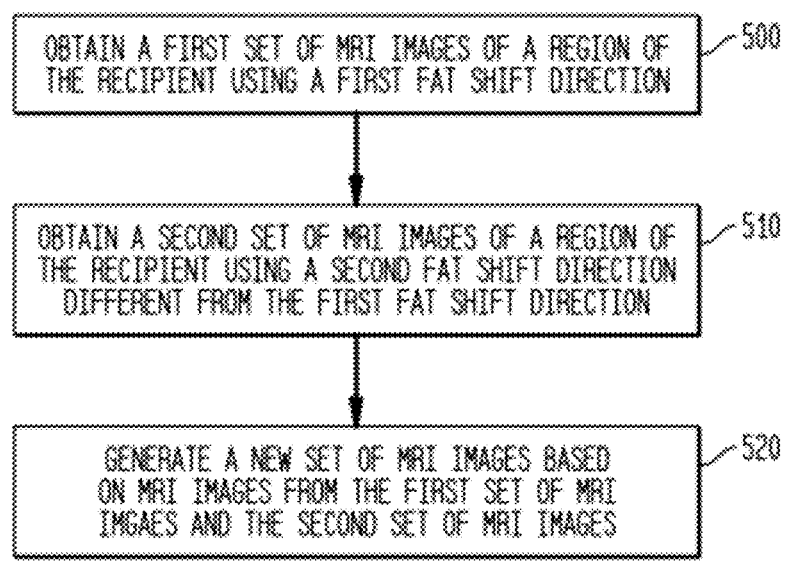
FIG. 10A shows a flow chart of a method described herein according to an embodiment of the present invention

An embodiment of the present invention includes a new T2W_TSE sequence in which parameters are adjusted from those of the standard sequence. An embodiment of the present invention includes a method utilizing a T2 weighted fast spin echo sequence, a widened receive bandwidth and right-left (R-L) phase encoding gradient direction. The following acquisition sequence may be used in some embodiments of the present invention as a baseline for acquiring images with a relatively minimal artifact: T2 weighted Fast Spin echo, ETL~19, Echo Spacing/Shot (ms)~10/190, Minimum voxel volume, for 5 mm slice thickness and/or Phase encoding gradient direction of R-L. An exemplary method includes scanning using a posterior (P) direction fat shift setting, and then repeating the scanning using an anterior (A) direction setting, and visa-versa FIG. 10A presents a flowchart for an exemplary method according to an embodiment of the present invention. At step 500, a first set of MRI images is obtained. This set is generated using a first fat shift direction. Step 500 may be executed using a specific scanning sequence, and may also encompass the use of data for a scan/sequence of scans previously performed by another party. In the method represented by the flowchart of FIG. 10A, at least some of the MRI images obtained in step 500 include an artifact caused by the presence of an implanted medical device such as a cochlear implant.

In step 510, a second set of MRI images of the same recipient is obtained. This set is generated using a second fat shift direction, different from the first fat shift direction used in step 500. The second fat shift direction may be approximately opposite the first fat shift direction. Step 510 may encompass actually generating the scan using a specific scanning sequence, and may also encompass obtaining data relating to a scan/sequence of scans previously performed by another party. This other party could be the same party that executed step 500 or could be a different party (e.g., the scan(s) may have been performed in a different MRI center, using for example, the same scan parameters but with an approximately opposite fat shift setting).

At least some of the MRI images produced or obtained in step 510 include an artifact resulting from the presence of the implant in the recipient, but the position of the artifact will be shifted in respective images due to the approximately opposite fat shift setting as previously described.

Proceeding to step 520, a new set of MRI images is produced based on MRI images from the first set of MRI images obtained in step 500 and the second set of MRI images obtained in step 510. As detailed above and as further detailed below with respect to FIG. 10B, step 520 may include selecting a sub-set of MRI images from the first set and a sub-set of MRI images from the second set such that the size of the artifact is reduced for at least some of the MRI images when compared to the MRI images including the artifact of first set and/or of the second set. In other embodiments, step 520 may include merging MRI image(s) of the first set and the second set of a given scan slice to generate a new MRI image(s), this new MRI image(s) replacing MRI image(s) of the first set and the second set having the artifact, thereby reducing the size of the artifact. In other embodiments of the present invention, some or all of the MRI images of the first set and/or the second set are subjected to image processing to reduce the size of the artifact in one or more of the MRI images of the first set and/or the second set. In yet other embodiments, at step 520, the artifact(s) of the MRI images are identified and replaced with computer generated images.

Figure 10B:
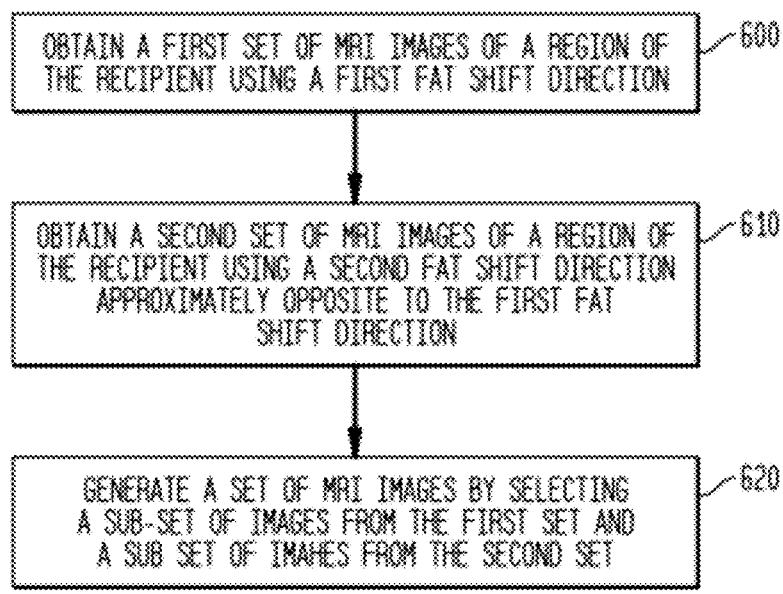
FIG. 10B shows a flow chart of a method described herein according to an embodiment of the present invention.

FIG. 10B presents a flowchart for an exemplary method according to an embodiment of the present invention. The method of FIG. 10B provides additional details to the method of FIG. 10A. At step 600, a first set of MRI images is obtained. This set is generated using a first fat shift direction (e.g., A). Step 600 may be executed using a specific scanning sequence, and may also encompass the use of data for a scan/sequence of scans previously performed by another party. In the method represented by the flowchart of FIG. 10B, at least some of the MRI images obtained in step 600 include an artifact caused by the presence of an implanted medical device such as a cochlear implant.

In step 610, a second set of MRI images of the same recipient is obtained. This set is generated using a second fat shift direction, approximately opposite to the first fat shift direction used in step 600 (e.g. P). Step 610 may encompass actually generating the scan using a specific scanning sequence, and may also encompass obtaining data relating to a scan/sequence of scans previously performed by another party. This other party could be the same party that executed step 600 or could be a different party (e.g., the scan(s) may have been performed in a different MRI center, using for example, the same scan parameters but with an approximately opposite fat shift setting).

At least some of the MRI images produced or obtained in step 610 include an artifact resulting from the presence of the implant in the recipient, but the position of the artifact will be shifted in respective images due to the approximately opposite fat shift setting as previously described.

Proceeding to step 620, a new set of MRI images is produced by selecting a sub-set of MRI images from the first set and a sub-set of MRI images from the second set such that the size of the artifact is reduced for at least some of the MRI images when compared to the MRI images including the artifact of first set and/or of the second set. Indeed, in some instances, the method represented by FIG. 10B will result in the artifact in the improved set having been completely eliminated. In other instances, some trace of the artifact may remain in the MRI images of the improved set, but the overall distortion is reduced.

Figure 10C:
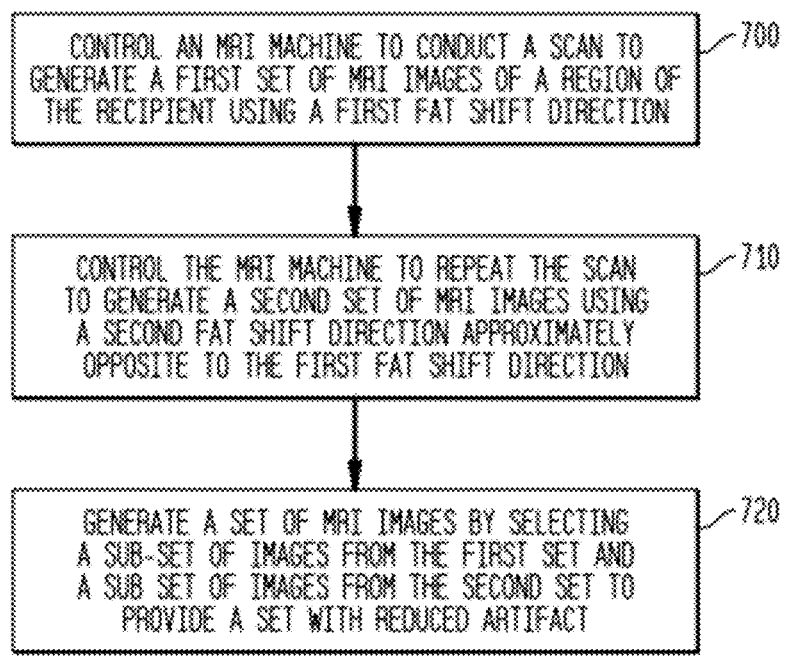
FIG. 10C shows a flowchart for a variation of the method of FIG. 10A according to an embodiment of the present invention.

FIG. 10C shows a flowchart for a method that is a variation of the method described with reference to FIG. 10B. This method may be executed to generate a set of MRI images of a recipient with an implanted medical device. At step 700, an operator controls an MRI machine to scan one or more slices, using a first fat shift direction (e.g., A), of a recipient of an implanted medical device, thereby generating a first set of MRI images of the recipient to generate a first set of MRI images. This first set comprises a plurality of MRI images including at least one MRI image comprising an artifact resulting from the implanted medical device.

Proceeding to step 710, the operator controls the MRI machine to repeat the scan of the one or more slices scanned at step 700, except using a fat shift direction approximately opposite to that used in step 700 (e.g., P), thereby generating a second set of MRI images. This second set comprises a plurality of images including at least one MRI image comprising the artifact, but shifted due to the reversed fat shift setting.

At step 720, a new set of MRI images is generated by selecting a sub-set of MRI images from the first set and a sub-set of MRI images from the second set of MRI images. The selection of step 720 is made such that the size/distortion effects of the artifacts of at least some of the MRI images of the resulting improved set are reduced (which, as used herein, includes eliminated) when compared with the artifacts of the first and/or second sets.

In some exemplary embodiments, the first set of MRI images and the second set of MRI images may have an equal number of corresponding images, and the step of selecting the sub-set of images from the first set and selecting the sub-set of images from the second set involves selecting at least one of the corresponding images with the smaller/less distorting artifact. By way of example, if MRI image 10 from the first set has a smaller (including no) artifact than image 10 from the second set, then image 10 from the first set is selected to form image 10 of the improved set.

In some exemplary methods, as noted above, the first and second MRI sets need not have the same number of MRI images. For example, if the first set has 20 MRI images and the second set has 22 MRI images, then a comparison may be made between "near corresponding" MRI images that may represent roughly the same region of the area scanned. For example, MRI image 10 of the first set 210 (MRI image set I) may roughly correspond to MRI image 9 of the second set and may be selected to form a set 200 (MRI image set III) of the same number of MRI images as one or the other of the first or second sets, or of yet another number, for example twenty-one MRI images.

In some exemplary embodiments of the present invention, the bandwidth of the receiver 420 of the MRI machine 401 is varied to provide improved results. In one example, the bandwidth is set to be greater than about 108 Hz/pix. In some exemplary embodiments, the bandwidth of the receiver 420 is set to about 233 Hz/pix. In another exemplary embodiment, the bandwidth is set to about 476 Hz/pix.

In another exemplary embodiment of the present invention, a single improved MRI image may be obtained, rather than a set of MRI images. By "improved," it is meant that of two MRI images obtained, at least one of those two MRI images having an artifact, the improved MRI image is the one with the smaller/less distorting artifact. In such an embodiment, the "smaller artifact" may be no artifact at all.

Figure 11:
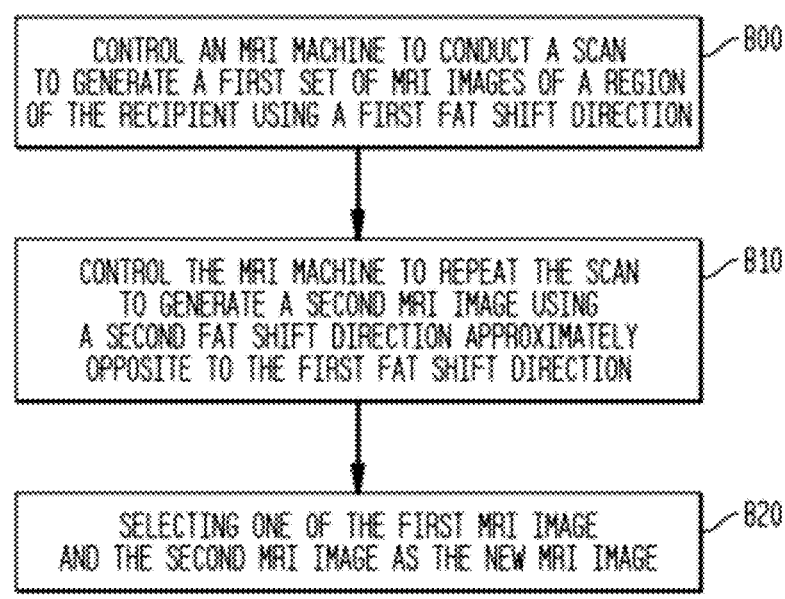
FIG. 11 shows a flowchart of a method of obtaining an MRI image according to an embodiment of the present invention.

FIG. 11 presents a flowchart for an exemplary method of obtaining an optimum MRI image of a recipient with a implantable medical device implanted in the recipient. In step 800, an MRI machine is controlled to scan the recipient and generate a first MRI image of the recipient using a first fat shift direction. At step 810, a determination is made whether or not the first MRI image includes an artifact resulting from the presence of the implantable medical device implanted in the recipient, and, if the determination is made in the affirmative, the MRI machine is controlled to repeat the scan using a second fat shift direction, approximately opposite to the first fat shift direction, to generate a second MRI image of the recipient. The method then proceeds to step 820, where whichever of the first MRI image or the second MRI image that has the smallest (or no) artifact is selected as the optimum MRI image.

It is noted that in some embodiments of the present invention, some or all of the above method steps of FIGS. 10A to 11 are executed automatically. In an exemplary embodiment, an MRI machine 400 or another device such as an image processor 450 that receives the MRI images, automatically evaluates the MRI images to determine which images have a reduced artifact, and generates a new set of MRI images based on the original set of MRI images according to the methods disclosed herein and variations thereof. In an exemplary embodiment, the MRI machine or the image processor 450 automatically ascertains which images for respective scan slices from various MRI image sets have a reduced distortion. By way of example, this may be done by automatically measuring the diameter of the artifacts of the MRI images and automatically selecting the MRI images where the artifact has the smaller diameter and/or disregarding the MRI images where the artifact has the larger diameter. In an exemplary embodiment of the present invention, the MRI machine 400 and/or the image processor 450 are configured to automatically execute some or all of the methods disclosed herein and variations thereof.

Figure 12A:
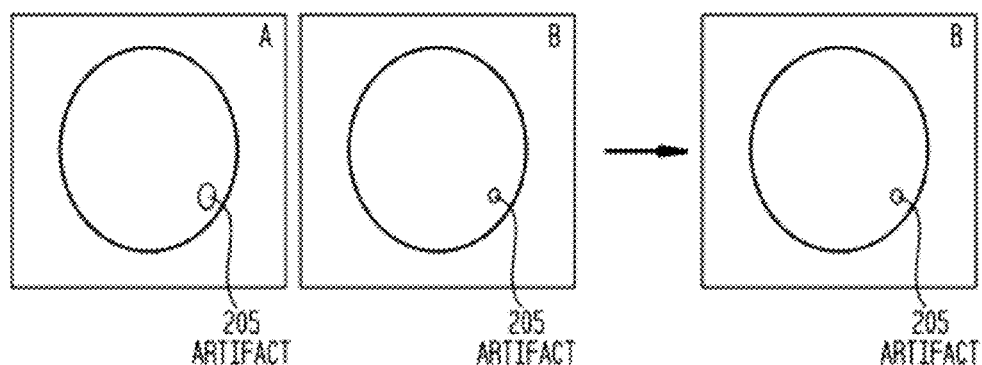
FIG. 12A shows first and second MRI images used in the method of FIG. 11.

FIG. 12A schematically depicts the MRI images of the method just described with reference to FIG. 11. FIG. 12A shows a first MRI image labeled "A" obtained from executing step 800 in the method described with reference to the flowchart of FIG. 11. An artifact 205 is may be seen in the MRI image labeled "A." As a result of executing step 810 of the method represented by FIG. 11, a second MRI image labeled "B" is obtained using the same scan sequence, but with the fat shift direction reversed (e.g., from A to P, or visa-versa). As a result of executing step 820 of the method represented by FIG. 11, the second MRI image labeled "B" is selected as the optimum MRI image since it has the smaller artifact 205. A specific example of the method represented by FIG. 11 may also be articulated with reference to FIGS. 3A-3E and 4A-4G. By way of example, a first MRI image is obtained according to the image of FIG. 3C upon executing step 800 and a second MRI image is obtained according to the image of FIG. 4C upon executing step 810, the image obtained by using a scan having an approximately opposite fat shift setting to that of the scan used to obtain the image of FIG. 3C. Because the artifact in FIG. 4C is smaller than the artifact in FIG. 3C, FIG. 4C is selected upon executing step 820 as the optimum MRI image. In this particular example, the first and second MRI images are taken as a series of MRI images, however, the images of FIGS. 3C and 4C could alternatively be obtained as individual MRI images and not obtained in a series. A further example may be seen with respect to the image of FIG. 3D (as the first MRI image) and the image of FIG. 4E (as the second MRI image). In this example, the image of FIG. 4E is selected upon executing step 820 as the optimum MRI image because the image of FIG. 4E has the smaller artifact.

Figure 12B:
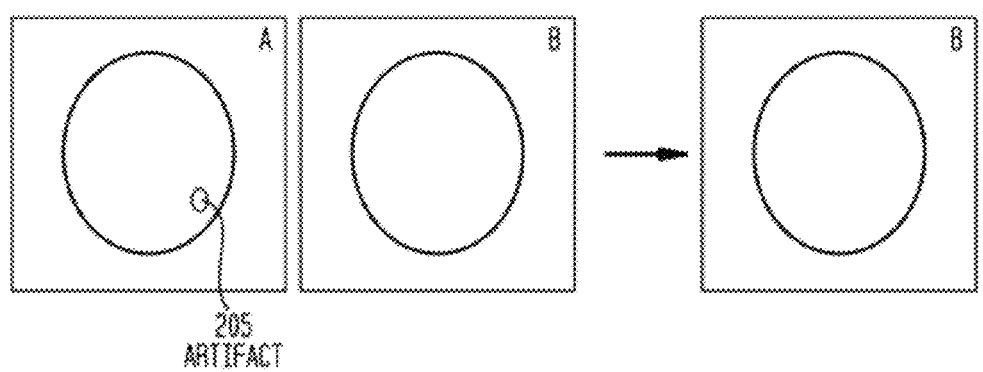
FIG. 12B shows another example of first and second MRI images used in the method of FIG. 11.
Figure 12C:
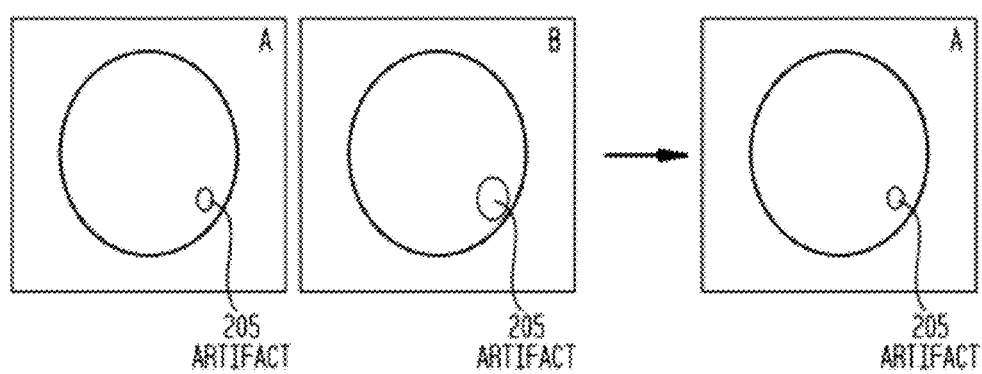
FIG. 12C shows yet another example of first and second MRI images used in the method of FIG. 11.

FIGS. 12B and 12C also schematically depict the MRI images of the method just described with reference to FIG. 11. In FIG. 12B, the first MRI image labeled "A" has an artifact 205, and the second MRI image labeled "B" has no artifact, and so the second MRI image labeled "B" is selected as the optimum MRI image upon the execution of step 820. In FIG. 12C, the first MRI image obtained by executing step 800 labeled "A" has an artifact 205, and so a second MRI image labeled "B" is obtained by proceeding to and executing step 810. In this example, the second MRI image labeled "B" has a larger artifact 205, and so the first MRI image labeled "A" is selected as the optimum MRI image upon the execution of step 820 because it has a smaller artifact 205 than that of second MRI image labeled "B."

Figure 13A:
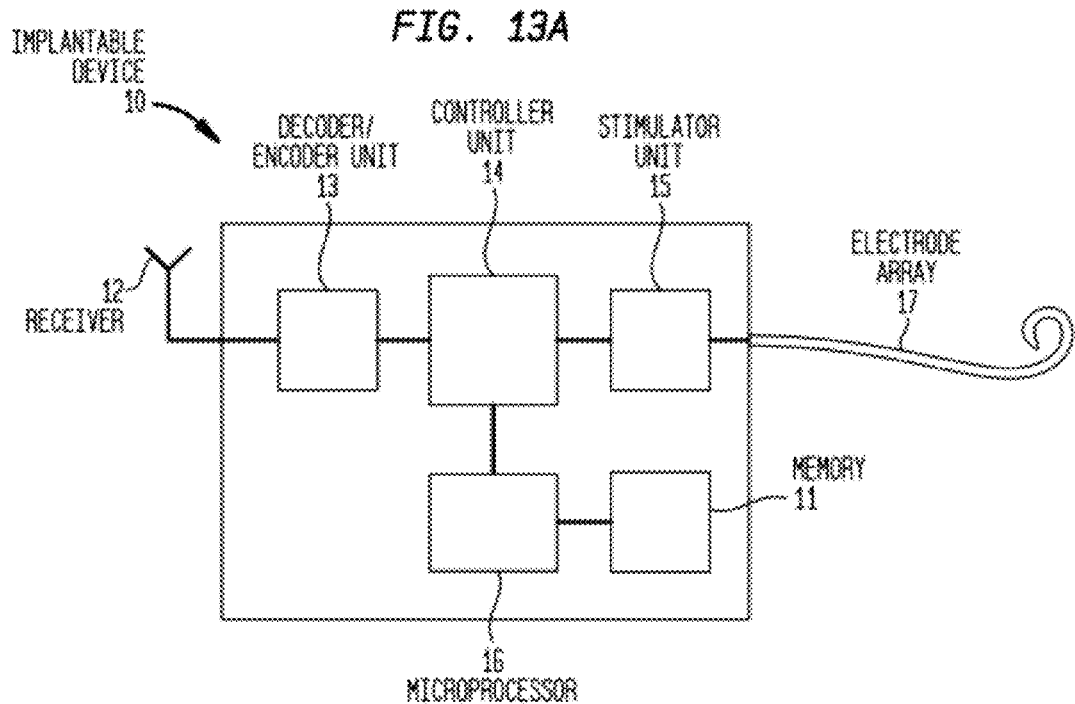
FIG. 13A shows a cochlear implant (CI) with instructions stored thereon to perform the method of FIGS. 10A, 10B and/or 11 according to an embodiment of the present invention.

FIG. 13A shows functional a block diagram of a implantable medical device, in this example, an implantable device 10 of a cochlear implant. Shown in FIG. 13A is an implantable device 10 (sometimes referred to as a receiver stimulator) of a cochlear implant comprising radio frequency (RF) receiver 12 for receiving RF signals from an external component 20 (see FIG. 13B, described below), a decoder/encoder unit 13, a controller unit 14, a stimulator unit 15, a microprocessor 16, a memory unit 11 and an electrode array 17.

In one exemplary embodiment of the present invention, the implantable device 10 of the cochlear implant has stored in its memory unit 11 instructions usable to direct an MRI machine and/or an operator of an MRI machine to carry out one or more of the methods described herein and variations thereof. These instructions are accessed and presented in a number of ways, including as a step-by-step instruction sheet or as a list of protocol and parameter settings. The instructions can be presented on a display screen that can interface with the cochlear implant, or printed on a printer, etc. Alternatively, the instructions can be presented as a sequence of audio instructions able to be heard by the operator through a speaker. Alternatively, these instructions may be read by an MRI machine.

The information on memory 11 is accessed via an external component 20 (see FIG. 18B) of a cochlear implant, or via another machine configured to interface with and interrogate implant 10, etc. In some embodiments of the present invention, the information just described is stored on memory 21 of external component 20 instead of or in addition to memory 11.

In some embodiments, the specific parameter settings are fine-tuned for the particular type of implanted medical device. For example, an implantable medical device might utilize an implantable battery which is supplied as a separate module. In such a scenario, there may be two (or more) modules (e.g., a main module and a battery module) positioned at different locations against the recipient's skill on the side of the recipient's head. By using transverse plane scans to obtain transverse plane MRI images as detailed above, it may not be possible to obtain MRI images which are free of artifact from either the main module or the battery module. This may be because the main and battery modules are located in separate transverse plane slices. According to an embodiment, a superior result may be obtained using a sequence of sagittal planes, at least if the main module and battery module are in similar sagittal planes.

Expanding on an embodiment briefly described above, in some embodiments of the present invention, the instructions on memory 11 and/or memory 21 (referring to FIGS. 13A and 13B, respectively) is in a machine-readable form to allow direct interface with a machine such as an MRI machine, to allow the machine to automatically carry out the scans in accordance with the methods described herein and variations thereof with the specific parameter values pre-programmed. As noted above, these specific parameter values are specific or fine-tuned for a specific type of implantable medical device.

Figure 13B:
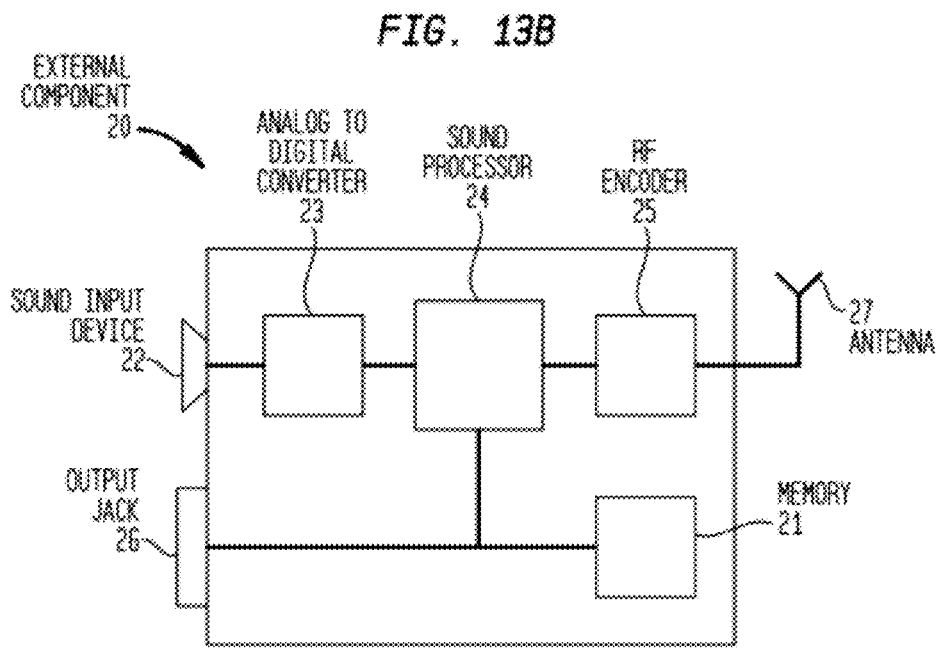
FIG. 13B shows a speech processor with instructions stored thereon to perform the method of FIGS. 10A, 10B and/or 11 according to an embodiment of the present invention.

FIG. 13B shows a block diagram of an external component 20 of a cochlear implant configured to control the implantable device 10 of FIG. 13A. External component 20 comprises a sound input device (e.g., microphone) 22, an analog to digital converter 23, a sound processor 24 configured to provide filter banks, sampling, amplitude mapping and/or general processing functions, and an RF encoder 25 for providing signals outputted by sound processor 24 to antenna 27 for transmission to implantable device 10. As noted above, also provided in external component 20 is memory 21, on which is stored instructions as described above.

FIG. 14 shows a cochlear implant 100, comprising implantable device 10 as described above in relation to FIG. 13A, and external component 20 as described above in relation to FIG. 13B in communication with one another.

In embodiments where instructions are stored in the memory 21 of external component 20 and/or stored in the memory 11 of implantable device 10 and accessed via external component 20, these instructions are accessed by any suitable device, system and/or method, such as, for example, any one or more of the output interfaces provided on a standard external component of a cochlear implant such as an output jack 26.

FIG. 15 shows a block diagram of a remote control unit 30 which is used in an embodiment of an implantable medical device. By way of example, remote control unit 30 is used to control implantable device 10 and/or external component 20. Remote control unit 30 comprises a recipient interface 31 which includes input keys or a voice control system, antenna 32 which transmits and/or receives wireless signals to and from the implantable device 10 and/or external component 20, and input-output jack 34 which is used to plug in a jack to connect the remote control unit 30 to a further machine to, for example, read status data, download and update software, and conduct other general maintenance of the implant system. Data is also read and/or downloaded wirelessly via antenna 32.

Remote control unit 30 also has a memory 33 on which may be stored thereon instructions to perform one or more of the methods described herein and variations thereof.

In some embodiments, the instructions are also stored on any other machine readable medium. For example, the instructions are stored on a hard disc, Digital Video Disc (DVD), Compact Disc (CD), memory stick, flash memory, RAM memory, ROM memory, EPROM memory or EEPROM memory. These stored instructions are then transferred at a later date from the machine readable medium to a device such as an implantable medical device such as a cochlear implant described herein and variations thereof, a remote control unit 30 for use with a cochlear implant or other hearing prosthesis, a printer, for printing out the instructions stored on the machine readable medium to be followed by an MRI machine operator, an MRI machine to enable it to carry our the methods automatically, or a display unit to display instructions to carry out the methods.

A reversing the fat shift setting in the method disclosed herein has the effect of shifting the position of the artifact by a limited amount, typically 25 mm, for a cochlear implant. Some embodiments include methods used in combination with other techniques to reduce MRI image artifact dimensions. Such may be done in the case where additional techniques reduce the artifact to less than the amount the artifact is shifted by the fat shift reversal. One example of a technique which could be used in combination with that described herein and variations thereof is the removal of a component, such as a coil locating magnet, from a cochlear implant. In this regard, it is noted that the MRI images shown in the figures herein with a cochlear implant were for a cochlear implant with a coil locating magnet removed.

Embodiments of the present invention are described herein primarily in connection with one type of hearing prosthesis, namely a cochlear prostheses (commonly referred to as cochlear prosthetic devices, cochlear implants, cochlear devices, and the like; simply "cochlea implants" herein.) Cochlear implants generally refer to hearing prostheses that deliver electrical stimulation to the cochlea of a recipient. As used herein, cochlear implants also include hearing prostheses that deliver electrical stimulation in combination with other types of stimulation, such as acoustic or mechanical stimulation. As discussed further below, it would be appreciated that some embodiments of the present invention may be variously implemented with respect to a recipient having any cochlear implant or other hearing prosthesis now known or later developed, including auditory brain stimulators, or implantable hearing prostheses that acoustically and/or mechanically stimulate components of the recipient's middle or inner ear.

Figure 16:
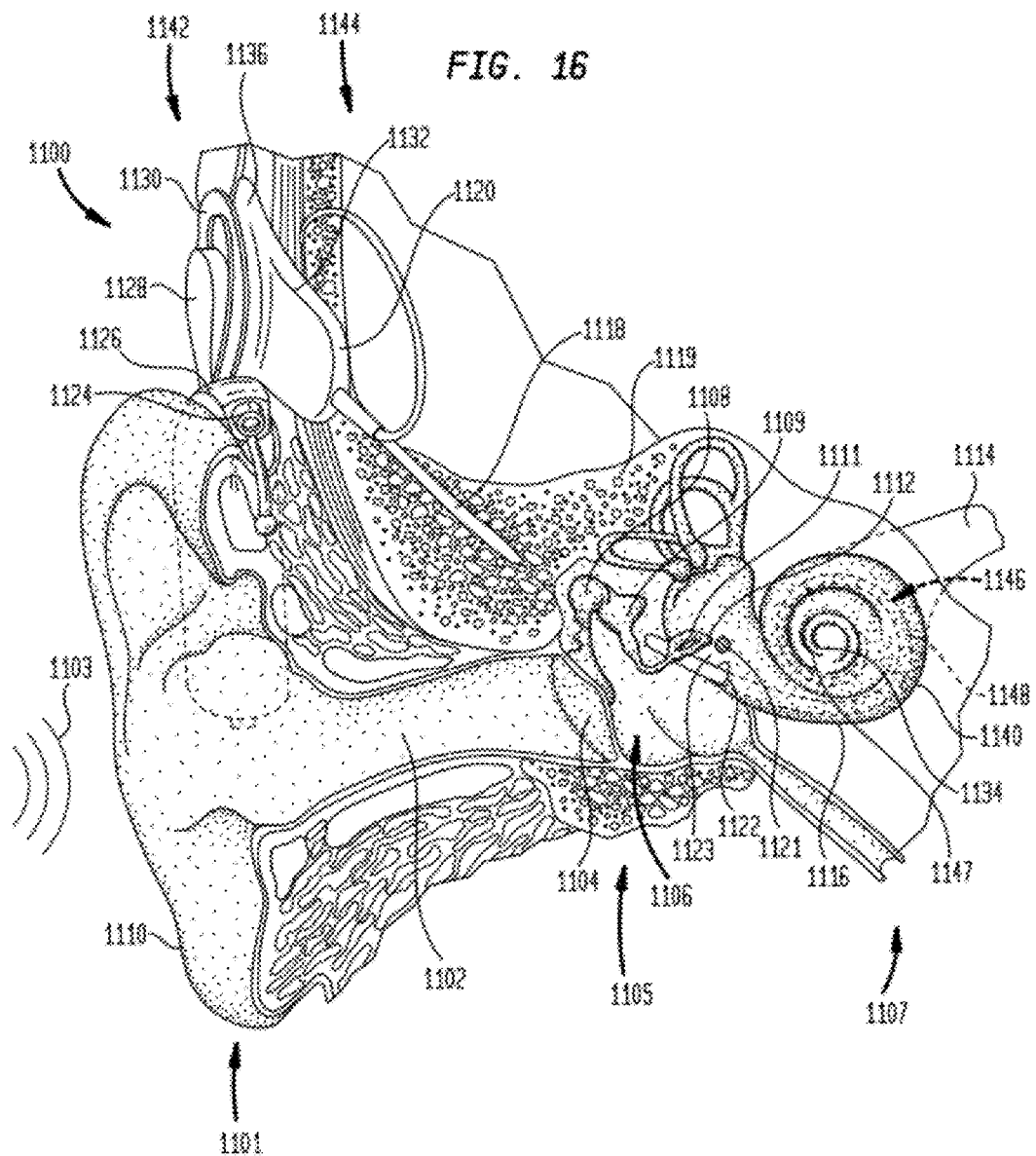
FIG. 16 shows a perspective view of a cochlear implant with which embodiments of the present invention may be implemented.

FIG. 16 is perspective view of a cochlear implant, referred to as cochlear implant 1100 implanted in a recipient. The recipient has an outer ear 1101, a middle ear 1105 and an inner ear 1107. Components of outer ear 1101, middle ear 1105 and inner ear 1107 are described below, followed by a description of cochlear implant 1100.

In a fully functional ear, outer ear 1101 comprises an auricle 1110 and an ear canal 1102. An acoustic pressure or sound wave 1103 is collected by auricle 1110 and channeled into and through ear canal 1102. Disposed across the distal end of ear cannel 1102 is a tympanic membrane 1104 which vibrates in response to sound wave 1103. This vibration is coupled to oval window or fenestra ovalis 1112 through three bones of middle ear 1105, collectively referred to as the ossicles 1106 and comprising the malleus 1108, the incus 1109 and the stapes 1111. Bones 1108, 1109 and 1111 of middle ear 1105 serve to filter and amplify sound wave 1103, causing oval window 1112 to articulate, or vibrate in response to vibration of tympanic membrane 1104. This vibration sets up waves of fluid motion of the perilymph within cochlea 1140. Such fluid motion, in turn, activates tiny hair cells (not shown) inside of cochlea 1140. Activation of the hair cells causes appropriate nerve impulses to be generated and transferred through the spiral ganglion cells (not shown) and auditory nerve 1114 to the brain (also not shown) where they are perceived as sound.

Cochlear implant 1100 comprises an external component 1142 (which, in some embodiments, corresponds to external component 20 detailed above) which is directly or indirectly attached to the body of the recipient, and an internal component 1144 (which, in some embodiments, corresponds to implantable device 10 detailed above) which is temporarily or permanently implanted in the recipient. External component 1142 typically comprises one or more sound input elements, such as microphone 1124 for detecting sound, a sound processor 1126, a power source (not shown), and an external transmitter unit 1128. External transmitter unit 1128 comprises an external coil 1130 and, preferably, a magnet (not shown) secured directly or indirectly to external coil 1130. Sound processor 1126 processes the output of microphone 1124 that is positioned, in the depicted embodiment, by auricle 1110 of the recipient. Sound processor 1126 generates encoded signals, sometimes referred to herein as encoded data signals, which are provided to external transmitter unit 1128 via a cable (not shown). Sound processor 1126 may further comprise a data input interface (not shown) that may be used to connect sound processor 1126 to a data source, such as a personal computer or musical instrument (e.g., a MIDI instrument).

Internal component 1144 comprises an internal receiver unit 1132, a stimulator unit 1120, and a stimulating lead assembly 1118. Internal receiver unit 1132 comprises an internal coil 1136, and preferably, a magnet (also not shown) fixed relative to the internal coil. Internal receiver unit 1132 and stimulator unit 1120 are hermetically sealed within a biocompatible housing, sometimes collectively referred to as a stimulator/receiver unit. The internal coil receives power and stimulation data from external coil 1130. Stimulating lead assembly 1118 has a proximal end connected to stimulator unit 1120, and a distal end implanted in cochlea 1140. Stimulating lead assembly 1118 extends from stimulator unit 1120 to cochlea 1140 through mastoid bone 1119. In some embodiments stimulating lead assembly 1118 may be implanted at least in basal region 1116, and sometimes further. For example, stimulating lead assembly 1118 may extend towards apical end of cochlea 1140, referred to as cochlea apex 1134. In certain circumstances, stimulating lead assembly 1118 may be inserted into cochlea 1140 via a cochleostomy 1122. In other circumstances, a cochleostomy may be formed through round window 1121, oval window 1112, the promontory 1123 or through an apical turn 1147 of cochlea 1140.

Stimulating lead assembly 1118 comprises a longitudinally aligned and distally extending array 1146 of electrode contacts 1148, sometimes referred to as array of electrode contacts 1146 herein. Although array of electrode contacts 1146 may be disposed on stimulating lead assembly 1118, in most practical applications, array of electrode contacts 1146 is integrated into stimulating lead assembly 1118. As such, array of electrode contacts 1146 is referred to herein as being disposed in stimulating lead assembly 1118. Stimulator unit 1120 generates stimulation signals which are applied by electrode contacts 1148 to cochlea 1140, thereby stimulating auditory nerve 1114. Because, in cochlear implant 1100, stimulating lead assembly 1118 provides stimulation, stimulating lead assembly 1118 is sometimes referred to as a stimulating lead assembly.

In cochlear implant 1100, external coil 1130 transmits electrical signals (that is, power and stimulation data) to internal coil 1136 via a radio frequency (RF) link. Internal coil 1136 is typically a wire antenna coil comprised of multiple turns of electrically insulated single-strand or multi-strand platinum or gold wire. The electrical insulation of internal coil 1136 is provided by a flexible silicone molding (not shown). In use, implantable receiver unit 1132 may be positioned in a recess of the temporal bone adjacent auricle 1110 of the recipient.

While the various aspects herein have been described with specific reference to a cochlear implant, it will be understood that the principles of the various aspects can be applied to reducing and/or eliminating the effects of artifact for other types of implantable medical devices, such as, for example:

ABIs (Auditory Brainstem Implants, which include electrodes placed in the auditory brainstem to enhance hearing) such as Cochlear Corporation's Nucleus 24 [R] Multichannel Auditory Brainstem Implant (Multichannel ABI).

The auditory brainstem implant consists of a small electrode that is applied to the brainstem where it stimulates acoustic nerves by means of electrical signals. The stimulating electrical signals are provided by a sound processor processing input sounds from a microphone located externally to the recipient. This allows the recipient to hear a certain degree of sound.

FES (Functional Electrical Stimulation) devices which are devices that utilize a technique that uses electrical currents to activate muscles and/or nerves, restoring function in people with paralysis-related disabilities.

SCS (Spinal Cord Stimulator) devices which, for example, deliver pulses of electrical energy via an electrode in the spinal area and can be used for pain management. An example of a commercially available system is the RESTOREPRIME system by Medtronic, Inc, USA.

The reference to any prior art in this specification is not, and should not be taken as, an acknowledgement of any form of suggestion that such prior art forms part of the common general knowledge.

While various embodiments of the present invention have been described above, it should be understood that they have been presented by way of example only, and not limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the following claims and their equivalents.

What is claimed is:

1. A method for generating a new set of MRI images of a region of a recipient in which an implanted medical device having magnetic properties is located, the method comprising:

scanning a plurality of scan slices of the recipient with an MRI machine set at a first fat shift direction resulting in a first set of MRI images including a plurality of MRI images respectively corresponding to the plurality of scan slices, wherein the first set of MRI images comprises at least one MRI image having an artifact resulting from the implanted medical device;

rescanning at least some of the plurality of scan slices with the MRI machine set at a second fat shift direction different than the first fat shift direction resulting in a second set of MRI images including at least one MRI image having an artifact resulting from the implanted medical device;

comparing a respective artifact of an MRI image corresponding to a first scan slice of the recipient of one of the first set of MRI images and the second set of MRI images to a respective artifact of an MRI image corresponding to the first scan slice of the recipient of the other of the first set of MRI images and the second set of MRI images; and selecting one of the compared MRI images based on the distortion to the respective MRI image created by the respective artifact.

2. The method of claim 1, wherein the action of rescanning at least some of the plurality of scan slices with the MRI machine set at a second fat shift direction approximately opposite to the first fat shift direction includes:

rescanning all of the plurality of scan slices.

3. The method of claim 1, wherein the action of rescanning at least some of the plurality of scan slices with the MRI machine set at a second fat shift direction approximately opposite to the first fat shift direction includes:

rescanning less than all of the plurality of scan slices.

4. The method of claim 1, wherein:

the first fat shift direction is a posterior direction and the second fat shift direction is an anterior direction.

5. The method of claim 1, wherein comparing the respective artifacts comprises:

comparing the size of the respective artifacts of an MRI image corresponding to the first scan slice of the recipient of one of the first set of MRI images and the second set of MRI images to a size of the respective artifact of the MRI image corresponding to the first scan slice of the recipient of the other of the first set of MRI images and the second set of MRI images.

6. The method of claim 5, wherein selecting one of the compared MRI image comprises:

determining based on the comparison which of the compared MRI images has a larger artifact; and discarding one of the compared MRI images having the larger artifact.

7. The method of claim 5, wherein selecting one of the compared MRI image comprises:

determining based on the comparison which of the compared MRI images has a smaller artifact; and selecting one of the compared MRI images having the smaller artifact.

8. The method of claim 1, further comprising creating the new set of MRI images by at least one of:
- replacing, in the first set of MRI images, the MRI image corresponding to the first scan slice of the recipient of the first set of MRI images with the MRI image corresponding to the first scan slice of the recipient of the second set of MRI images if the respective artifact imparts less distortion to the latter; or
- replacing, in the second set of MRI images, the MRI image corresponding to the first scan slice of the recipient of the second set of MRI images with the MRI image corresponding to the first scan slice of the recipient of the first set of MRI images if the respective artifact imparts less distortion to the latter.

9. A method of obtaining a new MRI image of a recipient of an implantable medical device, the method comprising:
- generating a first MRI image by scanning a first scan slice of the recipient with an MRI machine set at a first fat shift direction;
- generating a second MRI image by repeating the scan of the first scan slice with the MRI machine set at a second fat shift direction, approximately opposite to the first fat shift direction; and
- generating a new MRI image based on the first MRI image and the second MRI image.

10. The method of claim 9, wherein generating the new MRI image includes:
- selecting one of the first MRI image or the second MRI image as the new MRI image by selecting the MRI image with the smaller artifact resulting from the implantable medical device.

11. The method of claim 9, wherein generating the new MRI image includes:
- merging the first MRI image and the second MRI image to generate the new MRI image.

12. A method of obtaining a new MRI image of a recipient of an implantable medical device, the method comprising:
- repeating the method of claim 9 a plurality of times to obtain a new of improved MRI images.

13. A method for generating a set of MRI images of a region of a recipient in which an implanted medical device having magnetic properties is located, the method comprising:
- obtaining a first set of MRI images of the region of the recipient, the first set of MRI images comprising a plurality of MRI images obtained by MRI scanning a first plurality of scan slices of the recipient using a first fat shift direction, wherein at least one MRI image of the first set of MRI images includes an artifact resulting from the implanted medical device;
- obtaining a second set of MRI images, the second set of MRI images comprising a plurality of MRI images obtained by MRI scanning a second plurality of scan slices of the recipient using a second fat shift direction approximately opposite to the first fat shift direction, wherein at least a first scan slice of the second plurality of respective scan slices is the same scan slice as a scan slice of the first plurality of respective scan slices; and
- generating a third set of MRI images by selecting a sub-set of MRI images from the first set of MRI images and a sub-set of MRI images from the second set of MRI images and combining the sub-sets,
- wherein the third set includes an MRI image corresponding to the first scan slice, and
- wherein the size of the artifact of an MRI image of the third set corresponding to the first scan slice is reduced as compared to the size of the artifact of the MRI image of the first set of the first scan slice or the size of the artifact of the MRI image of the second set of the first scan slice.

14. The method of claim 13, wherein:
the action of selecting the sub-set of MRI images from the first set of MRI images and selecting the sub-set of MRI images from the second set of MRI images includes selecting, for the first scan slice, an MRI image from between the first set of MRI images and the second set of MRI images that has a smaller artifact.

15. The method of claim 13, wherein:
the action of selecting the sub-set of MRI images from the first set of MRI images and selecting the sub-set of MRI images from the second set of MRI images includes deleting, for the first scan slice, an MRI image from between the first set of MRI images and the second set of MRI images that has a larger artifact.

* * * * *